US010765741B2

(12) United States Patent
Markovic et al.

(10) Patent No.: US 10,765,741 B2
(45) Date of Patent: *Sep. 8, 2020

(54) METHODS FOR TREATING VEGF-EXPRESSING CANCER USING PREFORMED NANOPARTICLE COMPLEXES COMPRISING ALBUMIN-BOUND PACLITAXEL AND BEVACIZUMAB

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/225,428

(22) Filed: Aug. 1, 2016

(65) Prior Publication Data
US 2017/0106087 A1 Apr. 20, 2017

Related U.S. Application Data

(63) Continuation of application No. 14/116,619, filed as application No. PCT/US2012/037137 on May 9, 2012, now Pat. No. 9,427,477.

(60) Provisional application No. 61/609,689, filed on Mar. 12, 2012, provisional application No. 61/484,151, filed on May 9, 2011.

(51) Int. Cl.
| A61K 39/395 | (2006.01) |
| A61K 47/64 | (2017.01) |
| C07K 16/22 | (2006.01) |
| A61K 31/337 | (2006.01) |
| A61K 9/51 | (2006.01) |
| A61K 9/00 | (2006.01) |
| A61K 31/282 | (2006.01) |
| C07K 16/28 | (2006.01) |
| A61K 38/38 | (2006.01) |
| A61K 47/69 | (2017.01) |
| A61K 47/68 | (2017.01) |
| C07K 16/30 | (2006.01) |
| A61K 9/16 | (2006.01) |

(52) U.S. Cl.
CPC ...... *A61K 39/39558* (2013.01); *A61K 9/0019* (2013.01); *A61K 9/16* (2013.01); *A61K 9/5169* (2013.01); *A61K 31/282* (2013.01); *A61K 31/337* (2013.01); *A61K 38/38* (2013.01); *A61K 39/3955* (2013.01); *A61K 47/643* (2017.08); *A61K 47/6803* (2017.08); *A61K 47/6845* (2017.08); *A61K 47/6931* (2017.08); *C07K 16/22* (2013.01); *C07K 16/2887* (2013.01); *C07K 16/30* (2013.01)

(58) Field of Classification Search
None
See application file for complete search history.

(56) References Cited

U.S. PATENT DOCUMENTS

| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |

(Continued)

FOREIGN PATENT DOCUMENTS

| EP | 1 913 947 A1 | 4/2008 |
| EP | 3204413 | 8/2017 |

(Continued)

OTHER PUBLICATIONS

Lee, A, et al., "The co-delivery of paclitaxel and Herceptin using cationic micellar nanoparticles", Biomaterials Elsevier Science Publishers BV., Barking, GB, vol. 30, No. 5, Feb. 1, 2009, pp. 919-927.
Parker, Edward et al., "Targeting CLL Cells Using Ritumixab-Conjugated Surface Enhanced Raman Scattering (SERS) Gold Nanoparticles", Blood, American Society of Hematology, US, vol. 116, No. 21, Nov. 1, 2010, p. 1109.
"A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: <URL: https://clinicaltrials.gov/archive/NCT00434252/200703 12>, dated Mar. 12, 2007, 3 pages.

(Continued)

*Primary Examiner* — Laura B Goddard
(74) *Attorney, Agent, or Firm* — Myers Bigel, P.A.

(57) ABSTRACT

This document provides methods and materials related to treating cancer (e.g., skin cancer). For example, methods and materials relating to the use of a composition containing albumin-containing nanoparticle/antibody complexes (e.g., Abraxane®/anti-VEGF polypeptide antibody complexes) to treat cancer (e.g., skin cancer) are provided.

6 Claims, 17 Drawing Sheets

(56) References Cited

U.S. PATENT DOCUMENTS

| | | |
|---|---|---|
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,466,148 B2 | 10/2016 | Gay et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1* | 5/2010 | Desai .................. A61K 9/0019 424/499 |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0161819 A1 | 6/2014 | Hann et al. |
| 2014/0178486 A1 | 6/2014 | Markovic et al. |
| 2014/0155344 A1 | 8/2014 | Desai et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001-072589 | 3/2001 |
| KR | 1020090078330 | 7/2009 |
| RU | 2011133819 | 2/2013 |
| WO | WO-89/10398 A1 | 11/1989 |
| WO | WO-97/49390 A1 | 12/1997 |
| WO | WO-99/00113 A1 | 1/1999 |
| WO | WO-99/51248 A1 | 10/1999 |
| WO | 2004/022097 | 3/2004 |
| WO | WO-2004/096224 A2 | 11/2004 |
| WO | WO 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | WO-2008/057562 A1 | 5/2008 |
| WO | WO 2008/112987 * | 9/2008 |
| WO | WO-2008/112987 A1 | 9/2008 |
| WO | WO-2009/043159 A1 | 4/2009 |
| WO | WO-2009/055343 A2 | 4/2009 |
| WO | WO-2010/003057 A2 | 1/2010 |
| WO | WO-2010/017216 A2 | 2/2010 |
| WO | WO 2008/112987 * | 5/2010 |
| WO | 2010/118365 | 10/2010 |
| WO | 2010/124009 | 10/2010 |
| WO | WO 2010/136492 | 12/2010 |
| WO | WO-2012/048223 A1 | 4/2012 |
| WO | WO-2012/088388 A2 | 6/2012 |
| WO | WO-2012/154861 A2 | 11/2012 |
| WO | WO-2014/009774 | 1/2014 |
| WO | 2014/037422 | 3/2014 |
| WO | WO-2014/055415 A1 | 4/2014 |
| WO | 2014/105644 | 7/2014 |
| WO | WO-2014/123612 | 8/2014 |
| WO | 2015/048520 | 4/2015 |
| WO | WO-2015/191969 A1 | 12/2015 |
| WO | WO-2015/195476 A1 | 12/2015 |
| WO | 2016/059220 | 4/2016 |
| WO | WO-2016/057554 A1 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

(56) References Cited

FOREIGN PATENT DOCUMENTS

OTHER PUBLICATIONS

"Concurrent Infusions", J Oncol Pract., 4(4): 171, Jul. 2008.
AACR Presentation, "Targeted nano-immune conjugates to melanoma: Pre-clinical testing of bevacizumab targeted nab-paclitaxel," Mayo Clinic, 2014.
Abraxane® for Injectable Suspension (paclitaxel protein-bound particles for injectable suspension) (albumin-bound), [drug label], 22 pages, Sep. 2009.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen, TM, "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II , multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health , 2007, 4 pages.
Arakawa et al., "Protein-Solvent Interactions in Pharmaceutical Formulations", Pharm. Res., Mar. 1991, vol. 8, Issue 3, pp. 285-291.
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:S11-14.
Atkins, Michael, "Interleukin-2: clinical applications", Semin Oncol., 2002, 29(3 Suppl 7):12-27.
Avastin® Bevacizumab, Roche, [drug label], 24 pages, Sep. 2008.
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer, K., et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Boasberg et al., Nab-paclitaxel and bevacizumab as first-line therapy in patients with unresectable stage III and IV melanoma, J Clin Oncol., 27:15s, 2009 (suppl; abstr 9061), 2009 ASCO Annual Meeting, Retrieved from the Internet: <URL: http://meetinglibrary.asco.org/print/584876>, 2 pages, 2009.
Bolstad et al., "A comparison of normalization methods for high density oligonucleotide array data based on variance and bias", Bioinformatics, 2003, 19:185-193.

Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proc. Am. Soc. Clin. Oncol. 22: Abstract 2873 (2003).
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Davis, "Affinity separation of antibody-toxin conjugate from albumin-stabilized formulation", Am Biotechnol Lab., 12(4):60-64, Mar. 1994.
Degrasse, J.A., "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Folkman, J., "Angiogenesis in cancer, vascular, rheumatoid and other disease", Nat. Med., 1995, 1, 27-31.

(56) References Cited

OTHER PUBLICATIONS

Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Graells et al., "Overproduction of VEGF16s concomitantly expressed with its receptors promotes growth and survival of melanoma cells through MAPK and PI3K signaling", J. Invest. Dermatol., 2004, 123:1151-1161.
Gupta, I., et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin. Oncol., 2005, 23(16S):7558 (Abstract).
Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an antidigoxin single-chain Fv analogue produced in Escherichia coli", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2012/037137 dated Nov. 12, 2013, 5 pages.
International Preliminary Report on Patentability for Application No. PCT/US2008/057025, dated Sep. 15, 2009, 6 pages.
International Preliminary Report on Patentability for Application No. PCT/US2009/049511, dated Jan. 5, 2011, 6 pages.
International Preliminary Report on Patentability for Application No. PCT/US2013/062638, dated Apr. 16, 2015, 11 pages.
International Preliminary Report on Patentability, PCT/US2015/035505, Mayo Foundation for Medical Education and Research, 10 pages (Dec. 22, 2016).
International Preliminary Report on Patentability, PCT/US2015/035515, Mayo Foundation for Medical Education and Research, 18 pages. (Dec. 29, 2016).
International Search Report and Written Opinion for Application No. PCT/US15/35505 dated Nov. 24, 2015. 17 pages.
International Search Report and Written Opinion for Application No. PCT/US15/35515 dated Sep. 21, 2015. 23 pages.
International Search Report and Written Opinion for Application No. PCT/US16/47641 dated Oct. 31, 2016, 11 pages.
International Search Report and Written Opinion for Application No. PCT/US2008/057025, dated Jul. 1, 2008, 11 pages.
International Search Report and Written Opinion for Application No. PCT/US2009/049511, dated Feb. 2, 2010, 8 pages.
International Search Report and Written Opinion for Application No. PCT/US2012/037137 dated Sep. 28, 2012, 5 pages.
International Search Report and Written Opinion for Application No. PCT/US2013/062638, dated Jan. 23, 2014, 19 pages.
International Search Report and Written Opinion for Application No. PCT/US2015/054295 dated Jan. 25, 2016, 15 pages.
Jain et al., "Delivering nanomedicine to solid tumors", Nature Reviews Clinical Oncology, Nov. 7, 2010, pp. 653-664.
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther., (2003), 2:1183-1193.
Jiang et al., "Regulation of Immune Responses by T Cells", N Engl J Med., 2006, 354(11): 1166-1176.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kikuchi et al., "Vascular endothelial growth factor and dendritic cells in human squamous cell carcinoma of the oral cavity", Anticancer Res., 2006, 26(3A):1833-1848.
Kim et al., "A Dual Target-directed Agent against Interleukin-6 Receptor and Tumor Necrosis Factor a ameliorates experimental arthritis", Scientific Reports, 2016, pp. 1-12.
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curt Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.
Kratz et al., "Serum proteins as drug carriers of anticancer agents: a review", Drug Deliv., 5(4):281-299, 1998.

(56) References Cited

OTHER PUBLICATIONS

Kratz, "Albumin as a drug carrier: design of prodrugs, drug conjugates and nanoparticles", J Control Release, 132(3):171-183, Epub May 17, 2008.
Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.
Kukowska-Latallo et al., Nanoparticle Targeting of Anticancer Drug Improves Therapeutic Response in Animal Model of Human Epithelial Cancer, Cancer Res, 2005, 65(12):5317-5324.
Kumar et al., Th1/Th2 cytokine imbalance in meningioma, anaplastic astrocytoma and glioblastoma multiforme patients, Oncol. Rep., 2006, 15(6):1513-1516.
Lanzavecchia et al., "The use of hybrid hybridomas to target human cytotoxic T lymphocytes", Eur. J. Immunol., 1987, 17, pp. 105-111.
Lau et al., Is inhibition of cancer angiogenesis and growth by paclitaxel schedule dependent?, Anti-Cancer Drugs, 2004, 15:871-875.
Lei et al., Comparing cellular uptake and cytotoxicity of targeted drug carriers in cancer cell lines with different drug resistance mechanisms, Nanomed: Nanotech, Biol, and Med., 2011, 7:324-332.
Lev et al., Dacarbazine causes transcriptional up-regulation of interleukin 8 and vascular endothelial growth factor in melanoma cells: a possible escape mechanism from chemotherapy, Mol. Cancer Ther., 2003, 2:753-763.
Lev et al., Exposure of melanoma cells to dacarbazine results in enhanced tumor growth and metastasis in vivo, J. Clin. Oncol., 2004, 22:2092-2100.
Lin, S.Y, "Salmon calcitonin: conformational changes and stabilizer effects", AIMS Biophysics, 2015, 2(4): 695-723.
Marcoval et al., Angiogenesis and malignant melanoma. Angiogenesis is related to the development of vertical (tumorigenic) growth phase, J. Cutan. Pathol., 1997, 24:212-218.
Markovic et al., A phase II study of ABT-510 (thrombospondin-1 analog) for the treatment of metastatic melanoma, Am. J. Clin. Oncol., 2007, 30(3):303-309.
Markovic et al., A reproducible method for the enumeration of functional ( cytokine producing) versus non-functional peptide-specific cytotoxic T lymphocytes in human peripheral blood, Clin. Exo. Immunol., 2006, 145:438-447.
Markovic et al., Peptide vaccination of patients with metastatic melanoma: improved clinical outcome in patients demonstrating effective immunization, Am J Clin Oncol., 2006, 29(4):352-360.
Matejtschuk, P., "Lyophilization of Proteins", Methods in Molecular Biology, Cryopreservation and Freeze-Drying Protocols, Second Edition, Edited by: J. G. Day and G. N. Stacey © Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic: Paclitaxel Albumin-Stabilized Nanoparticle Formulation and Bevacizumab in Treating Patients With Stage IV Melanoma That Cannot Be Removed by Surgery—Full Text View ClinicalTrials.gov, Dec. 19, 2013, pp. 1-4, Retrieved from the Internet URL:https//clinicaltrials.gov/ct2/show/NCT02020707?term=targeted+nanoparticle+therapy+for+advanced+melanoma&rank=1 [retrieved on Jan. 6, 2016].
McElroy et al., Imaging of Primary and Metastatic Pancreatic Cancer Using a Fluorophore—Conjugated Anti-CA19-9 Antibody for Surgical Navigation, World J Surg., 2008, 32: 1057-1066.
Melcher, Recommendations for influenza and pneumococcal vaccinations in people receiving chemotherapy, Clin Oncol (R Coll Radiol), 2005, 17(1): 12-15.
Merchan et al., Increased endothelial uptake of paclitaxel as a potential mechanism for its antiangiogenic effects: potentiation by Cox-2 inhibition, Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", Sep. 2103, PLoS ONE vol. No. 8, Issue 9 pp. 1-10, e74216.
Middleton et al., Randomized phase III study of temozolomide versus dacarbazine in the treatment of patients with advanced metastatic malignant melanoma, J. Clin. Oncol., 2000, 18, pp. 158-166.
Miller et al. "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 56(6). pp. 761-770.
Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.
Mocellin et al., Cytokines and immune response in the tumor microenvironment, J Immunother., 2001, 24(5), pp. 392-407.
Motl, S., Bevacizumab in combination chemotherapy for colorectal and other cancers, Am. J. Health-Syst. Pharm 2005, 62:1021-1032.
Ng et al., Influence of formulation vehicle on metronomic taxane chemotherapy: albumin-bound versus cremophor EL-based paclitaxel, Clin. Cancer Res., 2006, 12, pp. 4331-4338.
Ng et al., Taxane-mediated antiangiogenesis in vitro: influence of formulation vehicles and binding proteins, Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Oku et al., Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts, Cancer Res., 1998, 58, pp. 4185-4192.
Parikh et al., The vascular endothelial growth factor family and its receptors, Hematol. Oncol. Clin. N. Am., 2004, 18, pp. 951-971.
Park et al., Anti-HER2 Immunoliposomes: Enhanced Efficacy Attributable to Targeted Delivery, Clin. Cancer Res., 2002, 8, pp. 1172-1181.
Perez et al., "Phase 2 trial of carboplatin, weekly paclitaxel, and biweekly bevacizumab in patients with unresectable stage IV melanoma," A north central cancer treatment group study, Cancer, 2009, 115(1), pp. 119-127.
Phase II: A Study of Bevacizumab With Carboplatin and Paclitaxel Chemotherapy for the First-Line Treatment of Patients With Metastatic Melanoma (BEAM) Mar 12, 2007, [retrieved Mar. 15, 2010]. Retrieved from the Internet: <URL:http://clinicaltrials.gov/archive/NCT00434252/2007 03 12>, 3 pages.
Pikal, M., Freeze-drying of proteins, Part II: Formulation selection, Biopharm, 1990, 9, pp. 26-30.
Polak et al., Mechanisms of local immunosuppression in cutaneous melanoma, Br J Cancer, 2007, 96(12), pp. 1879-1887.
Porrata et al., Early lymphocyte recovery predicts superior survival after autologous hematopoietic stem cell transplantation in multiple myeloma or non-Hodgkin lymphoma, Blood, 2001, 98(3), pp. 579-585.
Porrata et al., Timely reconstitution of immune competence affects clinical outcome following autologous stem cell transplantation, Clin Exp Med., 2004, 4(2):78-85.
Powell et al., Adoptive transfer of vaccine-induced peripheral blood mononuclear cells to patients with metastatic melanoma following lymphodepletion, J Immunol., 2006, 177(9), pp. 6527-6539.
Pries et al., Cytokines in head and neck cancer, Cytokine Growth Factor Rev., 2006, 17(3), pp. 141-146.
Ranieri et al., "Vascular endothelial growth factor (VEGF) as a target of bevacizumab in cancer: from the biology to the clinic", Curr. Med. Chem., 2006, 13, 1845-1857.
Rao et al., "Combination of paclitaxel and carboplatin as second-line therapy for patients with metastatic melanoma", Cancer, 2006, 106(2), 375-382.

(56) References Cited

OTHER PUBLICATIONS

Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.

Rosenberg et al., "Tumor progression can occur despite the induction of very high levels of self/tumor antigen-specific CD8+ T cells in patients with melanoma", J. Immunol., 2005, 175(9), pp. 6169-6176.

Roy et al., "Tumor associated release of interleukin-10 alters the prolactin receptor and down-regulates prolactin responsiveness of immature cortical thymocytes", J Neuroimmunol., 2007, 186(1-2), pp. 112-120.

Rudnicka et al., "Rituximab causes a polarization of B cells that augments its therapeutic function in NK-cell—mediated antibody-dependent cellular cytotoxicity", Blood, 2013, 121(23):4694-4702.

Sadat et al., "Nano-pharmaceutical Formulations for Targeted Drug Delivery against HER2 in Breast Cancer", Current Cancer Drug Targets, 2015, 15(1):71-86.

Salven et al., "Enhanced expression of vascular endothelial growth factor in metastatic melanoma", Br. J. Cancer, 1997, 76(7), pp. 930-934.

Sandler et al., "Paclitaxel-carboplatin alone or with bevacizumab for non-small-cell lung cancer", N. Engl. J. Med., 2006, 355:2542-2550.

Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.

Schrama et al., "Antibody targeted drugs as cancer therapeutics, Nature Reviews Drug Discovery", Feb. 2006, 5, pp. 147-159.

Sester et al., "Differences in CMV-specific T-cell levels and long-term susceptibility to CMV infection after kidney, heart and lung transplantation", Am J Transplant., 5(6):1483-1489, Jun 2005.

Srivastava et al., "Angiogenesis in cutaneous melanoma: pathogenesis and clinical implications", Microsc. Res. Tech., 2003, 60:208-224.

Streit et al., "Angiogenesis, lymphangiogenesis, and melanoma metastasis", Oncogene, 2003, 22, pp. 3172-3179.

Taieb et al., "Chemoimmunotherapy of tumors: Cyclophosphamide synergtizes with exosome based vaccines", J. Immunol., Mar. 1, 2006, 176(5):2722-2729.

Tao et al., "Inhibiting the growth of malignant melanoma by blocking the expression of vascular endothelial growth factor using an RNA interference approach", Br. J. Dermatol., 2005, 153:715-724.

Tas et al., "Circulating serum levels of angiogenic factors and vascular endothelial growth factor receptors 1 and 2 in melanoma patients", Melanoma Res., 2006, 16:405-411.

Terheyden et al., "Anti-vascular endothelial growth factor antibody bevacizumab in conjunction with chemotherapy in metastasizing melanoma", J Cancer Res Clin Oncol, 2007, 133(11), pp. 897-901.

Ugurel et al., "Increased serum concentration of angiogenic factors in malignant melanoma patients correlates with tumor progression and survival", J. Clin. Oncol., 2001, 19:577-583.

Vacca et al., "Docetaxel versus paclitaxel for antiangiogenesis", J. Hematother. Stem Cell Res., 2002, 11:103-118.

Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.

Vence et al., "Circulating tumor antigen-specific regulatory T cells in patients with metastatic melanoma", Proc Natl Acad Sci USA, 2007, 104(52), pp. 20884-20889.

Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.

Walker et al., "Monitoring immune responses in cancer patients receiving tumor vaccines", Int Rev Immunol., 2003, 22(3-4):283-319.

Wang et al., "Biofunctionalized targeted nanoparticles for therapeutic applications", Expert Opin. Biol. Ther., 2008, 8(8): 1063-1070.

Wang et al., "Paclitaxel at ultra low concentrations inhibits angiogenesis without affecting cellular microtubule assembly", Anti-Cancer Drugs, 2003, vol. 14, Issue 1, pp. 13-19.

Weber, "Review: anti-CTLA-4 antibody ipilimumab: case studies of clinical response and immune-related adverse events", Oncologist, Jul. 2007, 12(7), pp. 864-872.

Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.

Wong et al., "Programmed death-1 blockade enhances expansion and functional capacity of human melanoma antigen-specific CTLs", Int. Immunol., 2007, vol. 19, No. 10, pp. 1223-1234.

Wu et al., "Aptamers: Active Targeting Ligands for Cancer Diagnosis and Therapy", Theranostics, 2015, 5(4):322-344.

Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.

Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.

Yuan et al., "Vascular Permeability in a Human Tumor Xenograft: Molecular Size Dependence and Cutoff Size", Cancer Research, Sep. 1, 1995, 55, pp. 3752-3756.

Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.

Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).

Armitage, J.O. & Weisenburger, D.D. New approach to classifying non-Hodgkin's lymphomas: clinical features of the major histologic subtypes. Non-Hodgkin's Lymphoma Classification Project. J Clin Oncol 16, 2780-2795 (1998).

Bairagi et al., Albumin: A Versatile Drug Carrier, Austin Therapeutics, (Nov. 17, 2015) vol. 2, No. 2, p. 1021 (pp. 1-6), especially abstract, p. 2, Table 2, p. 2 col. 2 para. 2.

International Search Report and Written Opinion for Application No. PCT/US17/17553 dated May 3, 2017, 13 pages.

International Search Report and Written Opinion, PCT/US2017/023442, Mayo Foundation for Medical Education and Research, 8 pages (dated Jun. 16, 2017).

International Search Report and Written Opinion, PCT/US2017/023443, Mayo Foundation for Medical Education and Research, 10 pages (dated Jul. 11, 2017).

Jaime et al., "Paclitaxel antibody conjugates and trehalose for preserving the immunological activity after freeze-drying," Curr. Med. Chem., 11(4), pp. 439-446, Abstract Only (Feb. 2004).

Jin et al., "Paclitaxel-loaded nanoparticles decorated with anti-CD133 antibody: a targeted therapy for liver cancer stem cells," J. Nanopart. Res., 16:2157, 15 pages (Dec. 4, 2013).

Lundin et al., Phase 2 Study of Alemtuzumab (anti-CD52 Monoclonal Antibody) in Patients with Advanced Mycosis Fungoides/Sezary Syndrome, Blood. (Jun. 1, 2003) vol. 101, No. 11, pp. 4267-4272, especially p. 4267 col. 1, para. 1, p. 4267 col. 2, para 2-p. 4268 col. 1, para. 1, p. 4271 col. 1, para. 3.

Vishnu, P. et al., Safety and efficacy of nab-paclitaxel in the treatment of patients with breast cancer, Breast Cancer: Basic and Clinical Research, vol. 5, pp. 53-65 (2011).

Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL, http://sabcs.org/portals/sabcs2016/documents/sabcs-2015-abstracts.pdf?v=5.

(56) References Cited

OTHER PUBLICATIONS

Adams at al., "Phase lb trial of atezolizumab in combination with nab-paclitaxel in patients with metastatic triple-negative breast cancer (mTNBC)" Journal of Clinical Oncology col. 34, No. 15, May 1, 2016, 4 pages.
Anonymous, "A Phase III, Multicenter, Randomized Placebo-Controlled Study of Atezotizurnab (Anti-PD-L1 Antibody) in Combination with Nab Paclitaxel Compared with Placebo with Nab Paciltaxet for Patients with Previously Untreated Metastatic Triple Negative Breast Cancer", ClinicalTrials.gov, Apr. 21, 2015, 1 page.
Anonymous, "Atezolizumab Plus Abraxane Promising New Treatment for Triple-Negative Breast Cancer", UNM Comprehensive Cancer Center, Jan. 7, 2016. pp. 1-2.
U.S. Appl. No. 14/116,619, office action dated Feb. 4, 2015.
U.S. Appl. No. 14/116,619. office action dated Apr. 28, 2016.
U.S. Appl. No. 14/116,619, office action dated Sep. 10, 2015.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Feb. 9, 2018.
U.S. Appl. No. 15/052,336, office action dated Sep. 4, 2018.
U.S. Appl. No. 15/052,523, office action dated Feb. 9, 2018.
U.S. Appl. No. 15/052,623, office action dated May 19, 2017.
U.S. Appl. No. 15/052,623. office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/187,672, office action dated May 31, 2018.
U.S. Appl. No. 15/202,115, office action dated Jan. 20, 2017.
U.S. Appl. No. 15/202,115, office action dated Sep. 26, 2016.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,554, office action dated Sep. 27, 2018.
U.S. Appl. No. 15/412,564, office action dated Jul. 10, 2018.
U.S. Appl. No. 15/412,596, office action dated Sep. 4, 2018.
U.S. Appl. No. 15/412,610, office action dated Jul. 9, 2018.
U.S. Appl. No. 15/413,257; office action dated Sep. 25, 2018.
U.S. Appl. No. 15/414,536, office action dated Oct. 11, 2018.
U.S. Appl. No. 15/452,669, office action dated May 5, 2017.
U.S. Appl. No. 15/452,658, office action dated Nov. 16, 2017.
Baba, Oleo Science 10(1):15-18 (Jan. 2010).
Colman, "Effects of amino acid sequence changes on antibody-antigen interactions," Research in Immunology (145(1):33-36, (1994).
Desai et al., "Enhanced antitumor activity an safety of albumin-bound nab-docetaxel versus polysorbate 80-based docetaxel", Eur. J. Cancer, Suppl.; 18th Symposium on molecular targets and cancer therapeutics; Prague, Czech Republic; Nov. 7-10, 2006, vol. 4, No. 12, Nov. 2006 *Nov. 2006), p. 49.
Edison, "MorphoSys," 16 pages (Aug. 8, 2013).
Emens et al.: "(OT1-01-06) A phase III randomized trial of atezolizumab in combination with nab-paclitaxel as firs tline therapy for patienst with metastatic triple-negative breast cancer (mTNBC)", 2015, XP002775313, 2015 San Antonio Breast Cancer Symposium, URL: http://sabcs.org/portals/sabcs2016/documents/sabcs-2015-abbstracts.pdf?v=5.
European Application No. 08743903.0, Extended European Search Report dated Jan. 24, 2011.
European Application No. 09774506.1, Extended European Search Report dated Mar. 22, 2012.
European Application No. 12781802.9, Extendeo European Search Report dated Dec. 18, 2014.
European Application No. 13843209.1, Extended European Search Report dated Sep. 5, 2016.
European Application No. 15306443.6, Extended European Search Report dated Dec. 11, 2017.
European Application No. 15809075.3, Extended European Search Report dated Dec. 21, 2017.
Fabi et al, "Prospective study on nanoparticie albumin-bound paclitaael in advanced breast cancer: clinical results and biological observations in taxane-pretreated patients", Drug Design, Development and Therapy vol. 9, Nov. 1, 2015, 7 pages.
Flores et al., "Novel oral taxane therapies: recent Phase I results". Clin. Invest. vol. 3, No. 4, Apr. 1, 2013 (Apr. 1, 2013), pp. 333-341, XP055426571, UK, ISSN: 2041-6792, DOI. 10.4155/cli.13.18.
Golay et al., "Mechanism of action of therapeutic monoclonal antibodies: promises and pitfalls of in vitro and in vivo assay," Arch. Biochem. Biophys. 526(2):146-153 (2012).
Hamilton et al, "Nab-Pactitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthly 56(5):734-739 (May 2014).
Harlow et al., Antibodies. A Laboratory Manual, Cold Spring Harbor Laboratory, New York, 1988 (9 pages).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.
Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hood et al., Immunology, 1984, Benjamin, N.Y., 2nd edition.
Inman, "Atezolizumab/Nab-Paclitaxel Combo Shows High Response Rates in TNBC", OneLive, Dec. 10, 2015, 4 pages.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442 dated Oct. 4, 2018.
International Preliminary Report on Patentability for Application No. PCT/U52017/023443, dated Oct. 4, 2018.
International Preliminary Report on Patentability for Application PCT/US2016/026267, dated Apr. 10, 2018.
International Preliminary Report on Patentability for Application PCT/US2017/017553, dated Aug. 23, 2018.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2017/012580 dated Mar. 17, 2017.
International Search Report and Written Opinion for Application No. PCT/US2017/045643, dated Oct. 25, 2017.
International Search Report and Written Opinion for Application No. PCT/US2017/049745, dated Dec. 15, 2017.

(56) References Cited

OTHER PUBLICATIONS

International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355 dated Jan. 30, 2018.
Jain et al., "Normalizing tumor vasculature with anti-angiogenic therapy: a paradigm for combination therapy," Nat. Med. 7(9):987-989 (2001).
Jain, "Normalization of tumor vasculature: an emerging concept in antiangiogenic therapy," Science 307(5706):58-62 (2005).
Jin et al: "Docetaxel-loaded PEG-albumin nanoparticles with improved antitumor efficiency againt non-small cell lung cancer", Oncology Reports vol. 36, No. 2, Aug. 8, 2016 (Aug. 8, 2016), pp. 871-876, XP055425487, ISSN: 1021-335X, DOI:10.3892/or.2016.4863.
Kelly et al. "Shape-Specific, Monodisperse Nano-Molding of Protein Particles," J. Am. Chem. Soc. 130:5438-5439 (2008).
Liang et al., "IFN-alpha regulates NK cell cytotoxicity through STAT1 pathway," Cytokine, Aug. 13, 2003 (Aug. 13, 2003), vol. 23, pp. 190-199.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Meadows et al. "Anti-VEGF Therapies in the Clinic," Cold Spring Harbor Prespectives in Medicine, Oct. 1, 2012 (Oct. 1, 2012), vol. 2, pp.1-27.
Mustacchi et al, "The role of taxanes in triple-negative breast cancer: literature review". Drug Design, Development and Therapy, vol. 9, Aug. 5, 2015, 16 pages.
Nahleh et al, "Swog S0800 (NCI CDR0000636131): addition of bevacizumba to neoadjuvant nab-paclitaxel with dose-dense doxorubicin and cyclophosphamide improves pathologic complete response (pCR) rates in inflammatory or locally advanced breast cancer", Breast Cancer Research and Treatment. vol. 158, No. 3 Jul. 6, 2016, 12 pages.
Nevala et al, "Abstract B77: Targeted nano-immune conjugates to melanoma: Preclinical testing of bevacizumab targeted nab-paclitaxel", Cancer Immunology Research, vol. 3, Oct. 1, 2015, 3 pages.
Nevala et al, "Antibody-targeted paclitaxel loaded nanopartictes for the treatment of CD20 B-cell lymphoma", Scientific Reports, vol, 7, Apr. 5, 2017, 9 pages.
Nevala et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Nishida et al, English Translation of "Clinical Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
Ortaldo et al., "Effects of several species of human leukocyte interferon on cytotoxic activity c fNK cells and monocytes," International Journal of Cancer, Mar. 15, 1983 (Mar. 15, 1983) vol. 31, No. 3. pp. 285-289.
Ouichi, "Antibody delivery—from basics to clinical test—Clinical development of antibody-drug conjugate," Drug Deliv, Sys. 28(5). 424-429 (2013).
Petrelli et al., "Targeted Delivery for Breast Cancer Therapy: the History of Nanoparticle-Albumin-Bound Pactitaxel," Expert Opinion on Pharmacotherapy, Jun. 1, 2010 (Jun. 1, 2010), vol. 11, pp. 1413-32.
Qu Na et al: "Cabazitaxel-loaded human serum albumin nanoparticles as a therapeutic agent against prostate cancer", International Journal of Nanomedicine, vol. 11, Jul. 26, 2016 (Jul. 26, 2016), pp. 3451-3459.
Rudikoff et al., "Single amino acid substitution altering antigen-binding specificity," Proc Natl Acad Sci USA 1982 vol. 79 pp. 1979-1983.
Samaranayake et al., "Modified taxols. 5.1 Reactio of taxol with electrophilic reagents and preparation of a rearranged taxol derivatie with tubulin assembly activity", J. Org. Chem., col. 56, 1991, pp. 5114-5119.
Soda et al., "Latest topics of new medicine" Albumin-bound paclitaxel, Mol. Respiratory Di. 171(1):100-403 (Mar. 1, 2013).
Stancovski et al., "Mechanistic aspects of the opposing effects of monoclonal antivodies to the ERBB2 receptor on tumor growth," Proc Nati Acad Sci USA, 88: 8691-8695, (1991).
Terui, English Translation of Molecular-Targeted Therapy for Cancer Progresses and Challenges,"Daratumumab, Antibody Drug against Myeloma", Pharma Med., Nov. 10, 2013, vol. 31, No. 11, p. 27-30.
Volk et al , "Nab-paclitaxel efficacy in the orthotopic model of human breast cancer is significantly enhanced by concurrent anti-vascular endothelial growth factor A therapy." Neoplasia 10(613-623 (2008).
Volk-Draper et al, "Novel Model for Basaloid Triple negative Breast Cancer: Behavior In Vivo and Response to Therapy", vol. 14, No. 10, Oct. 1, 2012, 18 pages.
Washington University Schoot of Medione "Phase I/II Study of Abraxane in Recurrent and Refractory Lymphoma", ClinicalTrials.gov, Dec. 6, 2016, 7 pages.
Yu et al., "Interaction between bevacizumab and murine VEGF-A: a reassessment," Invest. Ophthalmol, Visual Sci. 49 (2): 522-527, Feb. 2008.
Yuan et al., "Time-dependent vascular regression and permeability changes in established human tumor xenografts induced by an ant-vascular endothelial growth factor/vascular permeability factor antibody." Proc. Natl. Acad. Sci. USA 93(25):14765-14770 (1996).
U.S. Appl. No. 14/432,979, office action dated Jan. 7, 2019.
U.S. Appl. No. 15/052,336, office action dated Jan. 22, 2019.
U.S. Appl. No. 15/052,623, office action dated Jan. 7, 2019.
U.S. Appl. No. 15/092,433, office action dated Dec. 12, 2018.
U.S. Appl. No. 15/157,672, office action dated Nov. 28, 2018.
U.S. Appl. No. 15/331,754; office action dated Feb. 22, 2019.
U.S. Appl. No. 15/412,536; office action dated Oct. 1, 2018.
U.S. Appl. No. 15/412,581, office action dated Mar. 8, 2019.
U.S. Appl. No. 15/412,581; office action dated Nov. 13, 2018.
U.S. Appl. No. 15/412,596, office action dated Dec. 27, 2018.
U.S. Appl. No. 15/412,610, office action dated Mar. 14, 2019.
U.S. Appl. No. 15/414,526, office action dated Mar. 12, 2019.
U.S. Appl. No. 15/414,526, office action dated Nov. 16, 2018.
U.S. Appl. No. 15/414,533; office action dated Mar. 8, 2019.
U.S. Appl. No. 15/414,533; office action dated Nov. 19, 2018.
U.S. Appl. No. 15/452,669, office action dated Nov. 26, 2018.
U.S. Appl. No. 15/456,377; office action dated Mar. 19, 2019.
U.S. Appl. No. 15/456,382; office action dated Mar. 18, 2019.
U.S. Appl. No. 15/456,391; office action dated Mar. 15, 2019.
U.S. Appl. No. 15/456,395; office action dated Mar. 28, 2019.
U.S. Appl. No. 15/456,399: office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization. pp. 10-18 (2004).
Cheng et al, Molecularly targeted drugs for metastatic colorectal cancer. Drug Des Devel Ther. Nov. 1, 2013 ;7 1315-22 (Year: 2013).
Elst et al. "Epidermal Growth Factor Receptor Expression and Activity in Acute Myeloid Leukemia", Blood 116:3144 (2010), abstract.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.

(56) References Cited

OTHER PUBLICATIONS

International Preliminary Report on Patentability for Application No. PCT/US2017/050137 dated Mar. 21, 2019.
Iqbal et al. Anti-Cancer Actions of Denosumab. Curr Osteoporos Rep. Dec. 2011;9(4): 173-6. (Year: 2011).
Lloyd et al. "Modelling the human immune response: performance of a 1011 human antibody repertoire against a broad panel of therapeutically relevant antigens", Protein Eng. , Design & Selection 22(3):159-168 (2009).
Matthay et al. Promising therapeutic targets in neuroblastoma. Clin Cancer Res. May 15, 2012;16(10)2740-53. (Year: 2012).
Reck et al. "Ipilimumab in combination with paclitaxel and carboplatin as first-line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents fot the treatment of chronic lymphocytic leukemia. Future Oneal. Jan. 2013;9(1):69-91, Abstract Only. (Year: 2013).
Verma et al. "Effect of surface properties on nanoparticle-cell interactions", Small. 6(1): 12-21. (2010).
Anonymous, "Phase I/II Study of Abraxane in Recurrent and Refractory Lymphoma", NCT01555853, ClinicalTrials.gov, Jun. 6, 2014 (8 pages).
Coiffier "The Role of Rituximab in Lymphomas", Rev. Bras. Hematol. Hemoter., 2002, vol. 24, No. 3, ISSN: 1516-8484 (6 pages).
U.S. Appl. No. 15/092,403, office action dated May 23, 2019.
U.S. Appl. No. 15/092,433, office action dated May 30, 2019.
U.S. Appl. No. 15/430,411, office action dated May 1, 2019.
Edwards et al. The Remarkable Flexibility of the Human Antibody Repertoire; Isolation of Over One Thousand Different Antibodies to a Single Protein, BLyS', J. Mol. Biol 334:103-116 (2003).
European Application No. 16637869.3, Extended European Search Report dated Apr. 4, 2019.
Package Insert, Campath® (ALEMTUZUMAB), Millennium and ILEX Partners, LP, 13 pages, available May 2001.
U.S. Appl. No. 15/187,672, office action dated Sep. 11, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/452,669: office action dated Jun. 24, 2019.
U.S. Appl. No. 15/456,377; office action dated Jul. 5, 2019.
U.S. Appl. No. 15/456,382; office action dated Jul. 8, 2019.
U.S. Appl. No. 15/456,395; office action dated Jul. 24, 2019.
U.S. Appl. No. 15/456,395: office action dated Aug. 14, 2019.
U.S. Appl. No. 15/456,399; office action dated Aug. 14, 2019.
U.S. Appl. No. 15/460,552; office action dated Aug. 14, 2019.
U.S. Appl. No. 15/460,699; office action dated Aug. 28, 2019.
U.S. Appl. No. 15/461,288; office action dated Aug. 28, 2019.
U.S. Appl. No. 15/752,155; office action dated Sep. 25, 2019.
Beers et al. "CD20 as a Target for Therapeutic Type I and II Monoclonal Antibodies", Seminars in Hematology 47 (2):107-114 (2010).
Belldegrun et al. "Human Renal Carcinoma Line Transfected with Interleukin-2 and/or Interferon alpha Gene(s): Implications for Live Cancer Vaccines", J National Cancer Institute 85(3)207-216 (1993).
Buechner "Intralesional interferon alfa-2b in the treatment of basal cell carcinoma", J Am Acad Dermatol 24:731-734 (1991).
Cirstoiu-Hapca et al, "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
Doveil et al. "Adjuvant Therapy of Stage IIIb Melanoma with Interferon Alfa-2b:Clinical and Immunological Relevance", Dermatology 191:234-239 (1995).
European Application No. 17736463.6, Extended European Search Report dated Jul. 8, 2019.
International Preliminary Report on Patentability for Application No. PCT/US2017/050134 dated Mar. 21, 2019.

Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-apha acquire mature dendritic and natural killer cell properties as shown by gene expression analysis", J Translated Medicine 5:46 (2007) (11 pages).
Liu et al. "Freeze-Drying of Proteins", In Walkers W., Oldenhof H. (eds) Cryopreservation and Freeze-Drying Protocols. Methods in Molecular Biology (Methods and Protocols), vol. 1257. Springer, New York, NY; published online Nov. 14, 2014.
European Application No. 17771005.0, Extended European Search Report dated Oct. 17, 2019.
European Application No. 17771006.8, Extended European Search Report dated Oct. 10, 2019.
U.S. Appl. No. 16/328,146; office action dated Feb. 26, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No. 17750912.2 Extended European Search Report dated Jan. 2, 2020.
Warner et al. "Alemtuzumab use in relapsed and refractory chronic lymphocytic leukemia: a history and discussion of future rational use", Ther Adv Hematol 3(6):375-389 (2012).
Anonymous "Paclitaxel Albumin-Stabilized Nanoparticie Formulation and Bevacizumab in Treating Patients With Stage IV Melanoma That Cannot Be Removed by Surgery or Gynecological Cancers". NCT02828707, ClinicalTrials.gov, Dec. 25, 2013 (13 pages).
U.S. Appl. No. 15/225,542, office action dated Jan. 14, 2020.
U.S. Appl. No. 15/286,024, office action dated Feb. 10, 2020.
U.S. Appl. No. 16/359,569; office action dated Jan. 17, 2020.
U.S. Appl. No. 15/430,411; office action dated Oct. 31, 2019.
U.S. Appl. No. 15/456,391; office action dated Feb. 4, 2020.
U.S. Appl. No. 15/675,596; office action dated Dec. 3, 2019.
U.S. Appl. No. 15/752,155; office action dated Feb. 7, 2020.
Miele et al. "Albumin-bound formulation of paclitaxel (Abraxane® ABI-007) in the treatment of breast cancer", International Journal of Nanomedicine 4:99-105 (2009).
Reynaldo et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).
Zhao et al. "Abraxane, the Nanoparticle Formulation of Paclitaxel Can Induce Drug Resistance by Ip-Regulation of P-gp", PLoS One 10(7):e0131429 (2015) (19 pages).
U.S. Appl. No. 14/116,619, filed Feb. 7, 2014.
U.S. Appl. No. 15/052,623, filed Feb. 24, 2016.
U.S. Appl. No. 14/432,979, filed Apr. 1, 2015.
U.S. Appl. No. 15/052,336, filed Feb. 24, 2016.
U.S. Appl. No. 15/187,672, filed Jun. 20, 2016.
U.S. Appl. No. 15/202,115, filed Jul. 5, 2016.
U.S. Appl. No. 15/413,257, filed Jan. 23, 2017.
U.S. Appl. No. 15/412,581, filed Jan. 23, 2017.
U.S. Appl. No. 15/412,564, filed Jan. 23, 2017.
U.S. Appl. No. 15/412,596, filed Jan. 23, 2017.
U.S. Appl. No. 15/412,610, filed Jan. 23, 2017.
U.S. Appl. No. 15/412,536, filed Jan. 23, 2017.
U.S. Appl. No. 15/412,554, filed Jan. 23, 2017.
U.S. Appl. No. 15/414,533, filed Jan. 24, 2017.
U.S. Appl. No. 15/414,536, filed Jan. 24, 2017.
U.S. Appl. No. 15/414,526, filed Jan. 24, 2017.
U.S. Appl. No. 14/882,327 U.S. Pat. No. 9,446,148, filed Oct. 13, 2015.
U.S. Appl. No. 15/060,967 U.S. Pat. No. 9,533,058, filed Mar. 4, 2016.
U.S. Appl. No. 15/060,912 U.S. Pat. No. 9,555,128, filed Mar. 4, 2016.
U.S. Appl. No. 15/064,396 U.S. Pat. No. 9,566,350, filed Mar. 8, 2016.
U.S. Appl. No. 15/331,754, filed Oct. 21, 2016.
U.S. Appl. No. 15/225,504, filed Aug. 1, 2016.

(56) References Cited

OTHER PUBLICATIONS

U.S. Appl. No. 15/225,542, filed Aug. 1, 2016.
U.S. Appl. No. 15/286,024, filed Oct. 5, 2016.
U.S. Appl. No. 15/286,006, filed Oct. 5, 2016.
U.S. Appl. No. 15/359,569, filed Nov. 22, 2016.
U.S. Appl. No. 15/456,377, filed Mar. 10, 2017.
U.S. Appl. No. 15/456,382, filed Mar. 10, 2017.
U.S. Appl. No. 15/456,391, filed Mar. 10, 2017.
U.S. Appl. No. 15/456,395, filed Mar. 10, 2017.
U.S. Appl. No. 15/456,399, filed Mar. 10, 2017.
U.S. Appl. No. 15/460,552, filed Mar. 16, 2017.
U.S. Appl. No. 15/460,699, filed Mar. 16, 2017.
U.S. Appl. No. 15/461,288, filed Mar. 16, 2017.
U.S. Appl. No. 14/116,619 U.S. Pat. No. 9,427,477, filed May 9, 2012.
U.S. Appl. No. 15/092,433, filed Apr. 6, 2016.
U.S. Appl. No. 15/092,403, filed Apr. 6, 2016.
U.S. Appl. No. 15/030,567, filed Apr. 19, 2016.
U.S. Appl. No. 15/452,669, filed Mar. 7, 2017.
U.S. Appl. No. 15/030,568, filed Apr. 19, 2016.
U.S. Appl. No. 15/430,411, filed Feb. 10, 2017.
Application No. 15/286,024, office action dated Jul. 29, 2020.
Application No. 15/675,596; office action dated May 28, 2020.
Application No. 16/328,146; office action dated Jul. 28, 2020.
Application No. 15/225,542; office action dated Jul. 30, 2020.

\* cited by examiner

METHODS FOR TREATING VEGF-EXPRESSING CANCER USING PREFORMED NANOPARTICLE COMPLEXES COMPRISING ALBUMIN-BOUND PACLITAXEL AND BEVACIZUMAB

CROSS-REFERENCE TO RELATED APPLICATIONS

This application is a continuation of U.S. patent application Ser. No. 14/116,619, filed Feb. 7, 2014, now U.S. Pat. No. 9,427,477, which is a National Stage application under 35 U.S.C. § 371 of International Application No. PCT/US2012/037137, filed May 9, 2012, which was published in English as International Publication No. WO2012/154861 and which claims the benefit of U.S. Provisional Application Ser. No. 61/609,689, filed Mar. 12, 2012, and U.S. Provisional Application Ser. No. 61/484,151, filed May 9, 2011. The disclosures of each of these prior applications is considered part of (and are incorporated by reference in its entirety in) the disclosure of this application.

BACKGROUND

1. Technical Field

This document relates to methods and materials involved in treating cancer (e.g., skin cancers such as melanoma). For example, this document relates to methods and materials involved in using complexes containing albumin-containing nanoparticles (e.g., Abraxane® nanoparticles) and antibodies (e.g., anti-VEGF polypeptide antibodies such as Avastin®) to treat cancer. This document also relates to methods and materials involved in using Abraxane® in combination with an anti-VEGF polypeptide antibody (e.g., Avastin®) to treat skin cancer.

2. Background Information

Melanoma is the most serious form of skin cancer. It is a malignant tumor that originates in melanocytes, the cells which produce the pigment melanin that colors skin, hair, and eyes and is heavily concentrated in most moles. While it is not the most common type of skin cancer, melanoma underlies the majority of skin cancer-related deaths. About 48,000 deaths worldwide are registered annually as being due to malignant melanoma. Worldwide, there are about 160,000 new cases of melanoma each year. Melanoma is more frequent in white men and is particularly common in white populations living in sunny climates. Other risk factors for developing melanoma include a history of sunburn, excessive sun exposure, living in a sunny climate or at high altitude, having many moles or large moles, and a family or personal history of skin cancer.

Melanomas fall into four major categories. Superficial spreading melanoma can travel along the top layer of the skin before penetrating more deeply. Lentigo maligna typically appears as a flat or mildly elevated mottled tan, brown, or dark brown discoloration and is found most often in the elderly. Nodular melanoma can occur anywhere on the body as a dark, protuberant papule or a plaque that varies from pearl to gray to black. Acral-lentiginous melanoma, although uncommon, is the most common form of melanoma in blacks. It can arise on palmar, plantar, or subungual skin. Metastasis of melanoma occurs via lymphatics and blood vessels. Local metastasis results in the formation of nearby satellite papules or nodules that may or may not be pigmented. Direct metastasis to skin or internal organs can occur.

SUMMARY

This document provides methods and materials involved in treating cancer (e.g., skin cancers such as melanoma). For example, this document provides methods and materials for using complexes containing albumin-containing nanoparticles (e.g., Abraxane® nanoparticles) and antibodies (e.g., anti-VEGF polypeptide antibodies such as Avastin®) to treat cancer. This document also provides methods and materials involved in using Abraxane® in combination with an anti-VEGF polypeptide antibody (e.g., Avastin®) to treat skin cancer (e.g., melanoma). Abraxane® is available from Celgene Corp. and is a nanoparticle formulation that combines paclitaxel with human albumin. Avastin® is also known as bevacizumab and is available from Genentech Corp. and Roche Corp. Avastin® is a humanized monoclonal antibody that binds to vascular endothelial growth factor A. As described herein, in vitro mixing of albumin-containing nanoparticles (e.g., Abraxane® nanoparticles) and antibodies (e.g., bevacizumab, bevacizumab, trastuzamab, or rituxan) can result in the formation of macromolecular complexes, the characteristics of which (e.g., size, antibody content, or chemotherapeutic drug content) can be customized depending on need. In some cases, such macromolecular complexes can retain antibody mediated target binding specificity, can retain or exhibit enhanced chemotherapeutic tumor cell cytotoxicity, and can exhibit no additional toxicity beyond that of Abraxane® nanoparticles alone. As also described herein, contacting Abraxane® with an anti-VEGF polypeptide antibody (e.g., Avastin®) prior to administration to a human (e.g., a human melanoma cancer patient) can result in a complex that, when administered as a complex, has an increased ability to treat melanoma as compared to a treatment regimen that includes administering Abraxane® and the anti-VEGF polypeptide antibody separately in a manner that does not form Abraxane®/anti-VEGF polypeptide antibody complexes.

The methods and materials provided herein can be used to increase the progression-free survival rate in skin cancer patients. Increasing progression-free survival can allow skin cancer patients to live longer.

In general, one aspect of this document features a method for treating a mammal having skin cancer. The method comprises, or consists essentially of, administering to the mammal a composition containing Abraxane®/anti-VEGF polypeptide antibody complexes (or complexes of (a) an anti-VEGF polypeptide antibody and (b) human albumin-containing nanoparticles having an agent other than placitaxel) under conditions wherein the length of progression-free survival is increased. The mammal can be a human. The skin cancer can be melanoma. The skin cancer can be stage IV melanoma. In some cases, a composition comprising Abraxane®/Avastin® complexes can be administered to the mammal. The composition can comprise an alkylating agent. The alkylating agent can be a platinum compound. The platinum compound can be carboplatin. The anti-VEGF polypeptide antibody can be a humanized antibody. The anti-VEGF polypeptide antibody can be bevacizumab. The composition can be administered by injection. The progression-free survival can be increased by 25 percent. The progression-free survival can be increased by 50 percent. The progression-free survival is increased by 75 percent. The progression-free survival can be increased by 100 percent. The composition can be administered under conditions wherein the time to progression is increased.

In another aspect, this document features a method for treating a mammal having cancer. The method comprises, or consists essentially of, administering, to the mammal, a composition comprising albumin-containing nanoparticle/antibody complexes, wherein the average diameter of the complexes is greater than 1 μm (e.g., between 1.1 μm and 5 μm, between 1.5 μm and 5 μm, between 4.5 and 20 μm, or between 5 and 20 μm). The mammal can be a human. The cancer can be skin cancer. The skin cancer can be melanoma. The skin cancer can be stage IV melanoma. The albumin-containing nanoparticle/antibody complexes can be Abraxane®/Avastin® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of the complexes can be from 1.1 μm to 5 μm. The average diameter of the complexes can be from 2 μm to 5 μm. The average diameter of the complexes can be from 3 μm to 5 μm. The average diameter of the complexes can be from 5 μm to 50 μm. The average diameter of the complexes can be from 10 μm to 50 μm. The average diameter of the complexes can be from 5 μm to 25 μm.

In another aspect, this document features a method for treating a mammal having cancer. The method comprises, or consists essentially of, administering, to the mammal, a composition comprising albumin-containing nanoparticle/antibody complexes, wherein the average diameter of at least 5 percent of the complexes of the composition is greater than 1 μm. The mammal can be a human. The cancer can be skin cancer. The skin cancer can be melanoma. The skin cancer can be stage IV melanoma. The albumin-containing nanoparticle/antibody complexes can be Abraxane®/Avastin® complexes. The composition or the albumin-containing nanoparticle/antibody complexes can comprise an alkylating agent. The alkylating agent can be a platinum compound. The platinum compound can be carboplatin. The antibodies of the albumin-containing nanoparticle/antibody complexes can be anti-VEGF polypeptide antibodies. The anti-VEGF polypeptide antibodies can be humanized antibodies. The anti-VEGF polypeptide antibodies can be bevacizumab. The composition can be administered by injection. The administration of the composition can be effective to increase progression-free survival by 25 percent. The administration of the composition can be effective to increase progression-free survival by 50 percent. The administration of the composition can be effective to increase progression-free survival by 75 percent. The administration of the composition can be effective to increase progression-free survival by 100 percent. The administration of the composition can be under conditions wherein the median time to progression for a population of mammals with the cancer is at least 150 days. The administration of the composition can be under conditions wherein the median time to progression for a population of mammals with the cancer is at least 165 days. The administration of the composition can be under conditions wherein the median time to progression for a population of mammals with the cancer is at least 170 days. The average diameter of at least 5 percent of said complexes of said composition can be from 1.1 μm to 5 μm. The average diameter of at least 5 percent of said complexes of said composition can be from 2 μm to 5 μm. The average diameter of at least 5 percent of said complexes of said composition can be from 3 μm to 5 μm. The average diameter of at least 5 percent of said complexes of said composition can be from 5 μm to 50 μm. The average diameter of at least 5 percent of said complexes of said composition can be from 10 μm to 50 μm. The average diameter of at least 5 percent of said complexes of said composition can be from 5 μm to 25 μm. The average diameter of at least 10 percent of said complexes of said composition can be greater than 1 μm. The average diameter of at least 50 percent of said complexes of said composition can be greater than 1 μm. The average diameter of at least 75 percent of said complexes of said composition can be greater than 1 μm. The average diameter of at least 90 percent of said complexes of said composition can be greater than 1 μm.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

In FIG. 4, 100 ng VEGF was used to visualize the complex.

FIG. 16 contains graphs of the size distributions of the indicated complexes incubated for the indicated time.

DETAILED DESCRIPTION

Figure 1:
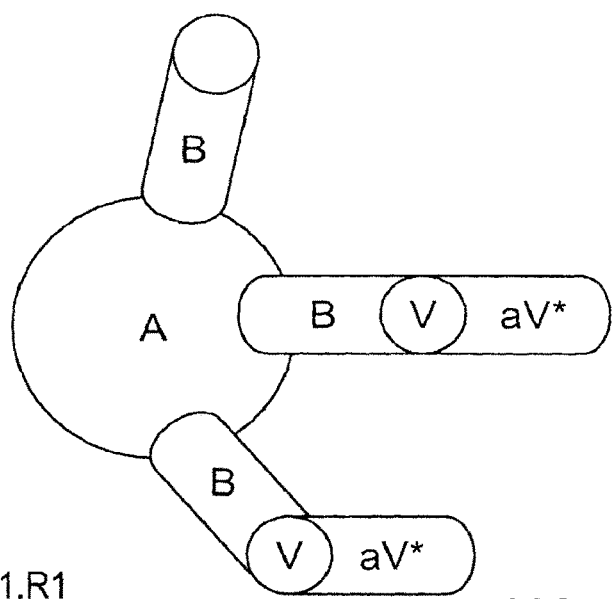
FIG. 1 is a diagram of an Abraxane® nanoparticle (labeled A) complexed with an anti-VEGF polypeptide antibody (bevacizumab; labeled B). In two of the three cases, the anti-VEGF polypeptide antibody is shown binding to a VEGF-A polypeptide (labeled V), and a fluorescently-labeled anti-VEGF antibody (labeled aV*) is shown bound to the VEGF-A polypeptide.
Figure 2:
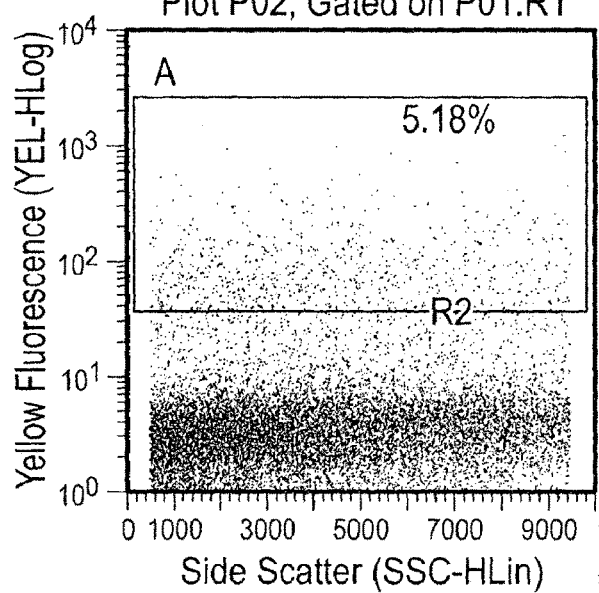
FIG. 2 contains scatter plots of a flow cytometry analysis plotting the level of yellow fluorescence of A alone, A plus aV*, A plus B plus aV*, A plus V plus aV*, or A plus B plus V plus aV*. The labels are as indicated in FIG. 1. These results demonstrate that A and B spontaneously associate and preserve a VEGF polypeptide binding potential.
Figure 2:
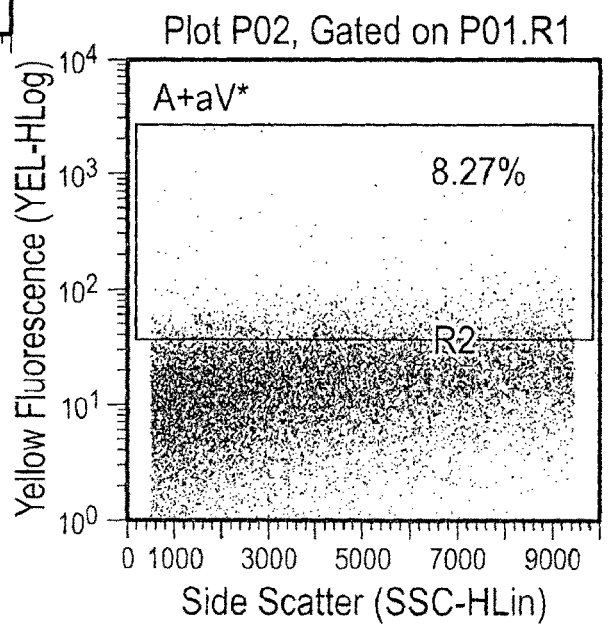
Figure 2:
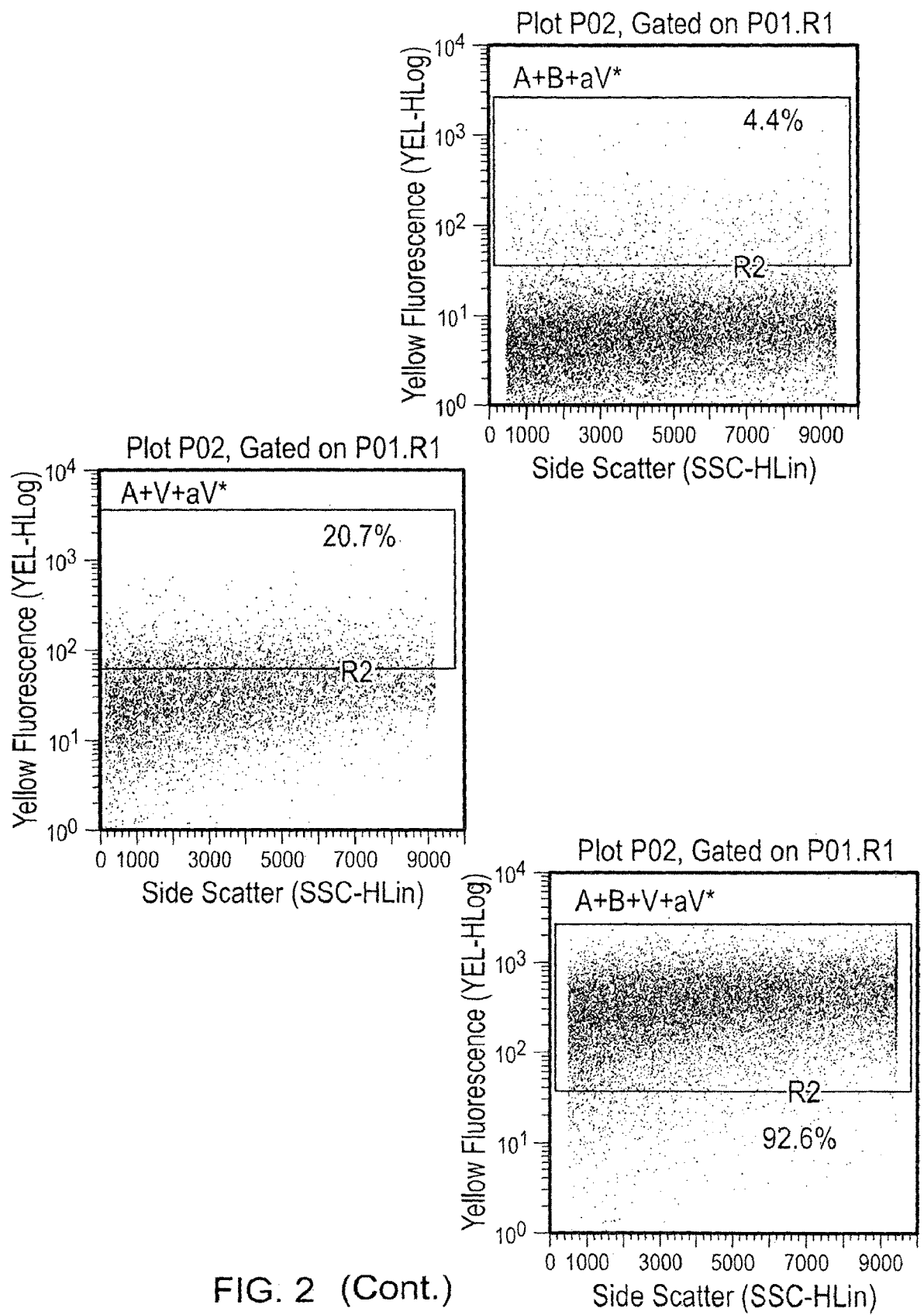
Figure 3:
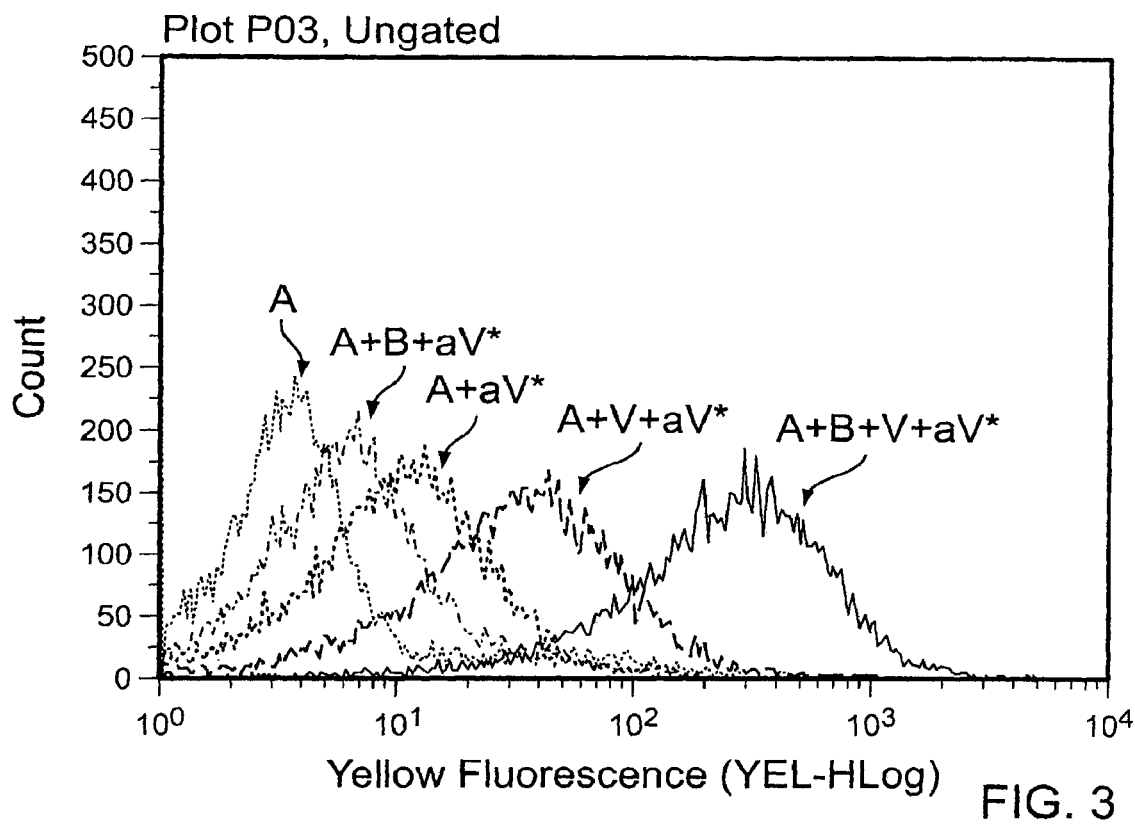
FIG. 3 is graph that contains the flow cytometry data from FIG. 2.
Figure 4:
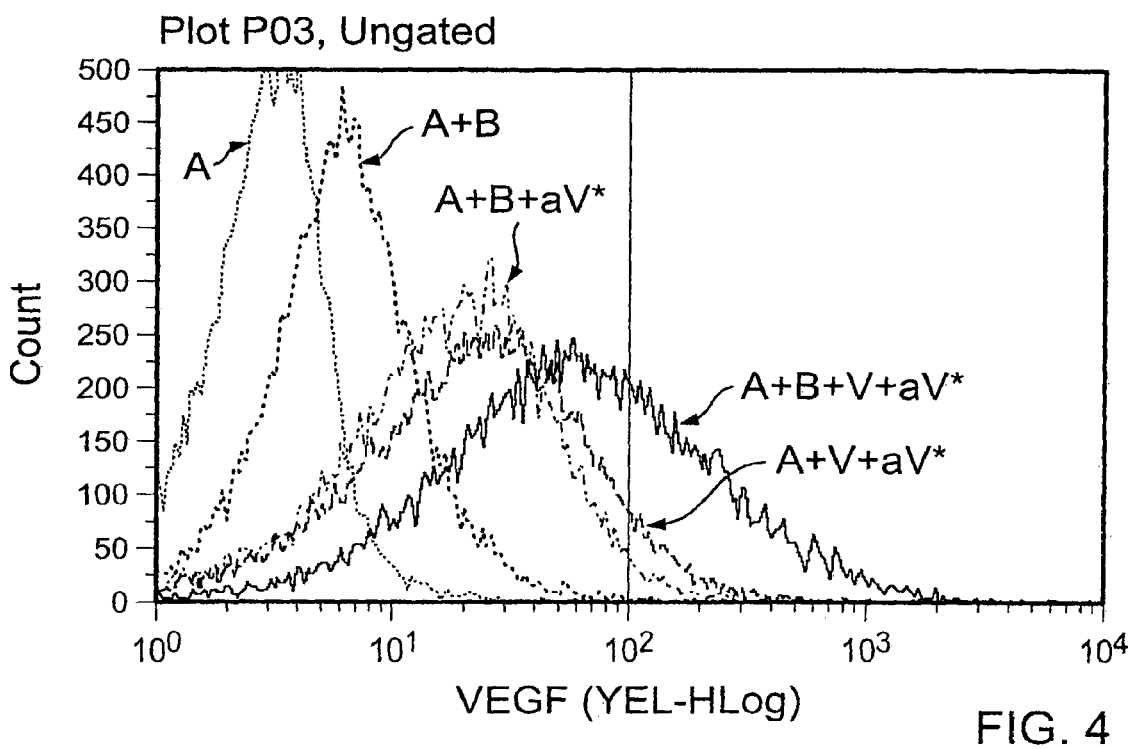
FIG. 4 is a repeat of the experiment of FIG. 3, comparing A alone, A plus aV*, A plus B plus aV*, A plus V plus aV*, or A plus B plus V plus aV*. One difference is in FIG. 3, 500 ng of VEGF was used.
Figure 5:
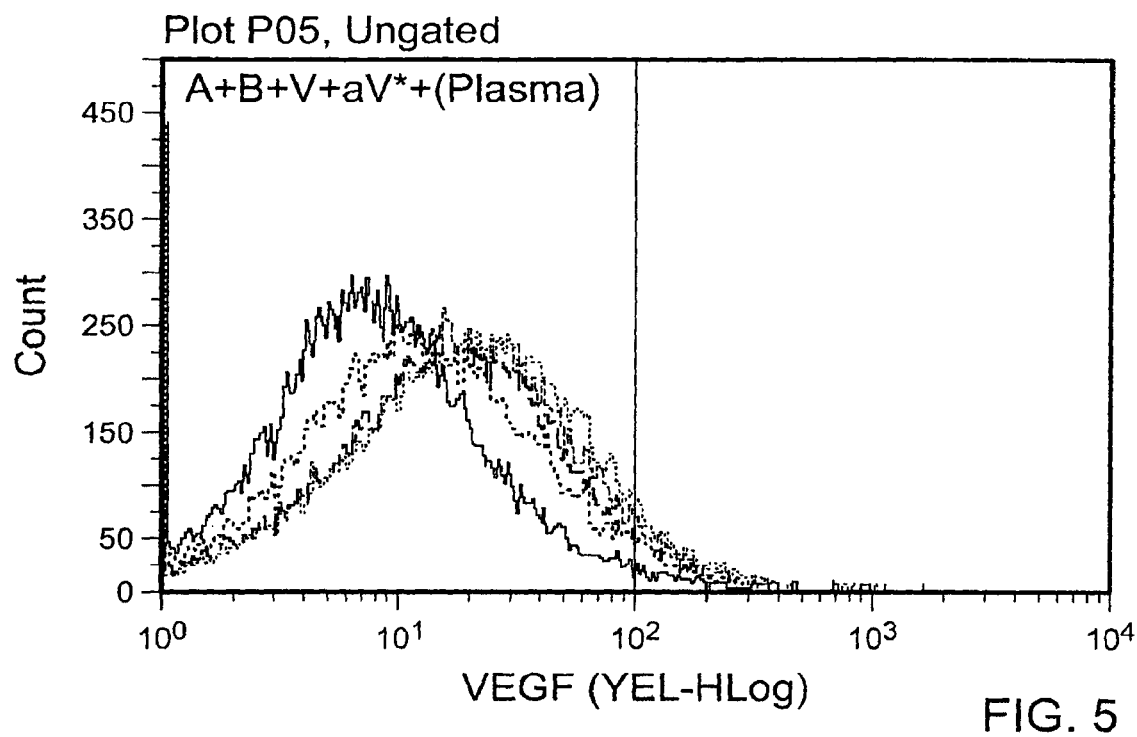
FIG. 5 is a graph plotting flow cytometry data of A plus B incubated in the presence of various concentrations of human plasma (1:1 to 1:16) followed by addition of V and aV*. These results indicate that human plasma diluted in a range of relative volumes (1:1 to 1:16) successfully inhibited the formation of the A+B complex relative to controls.
Figure 6:
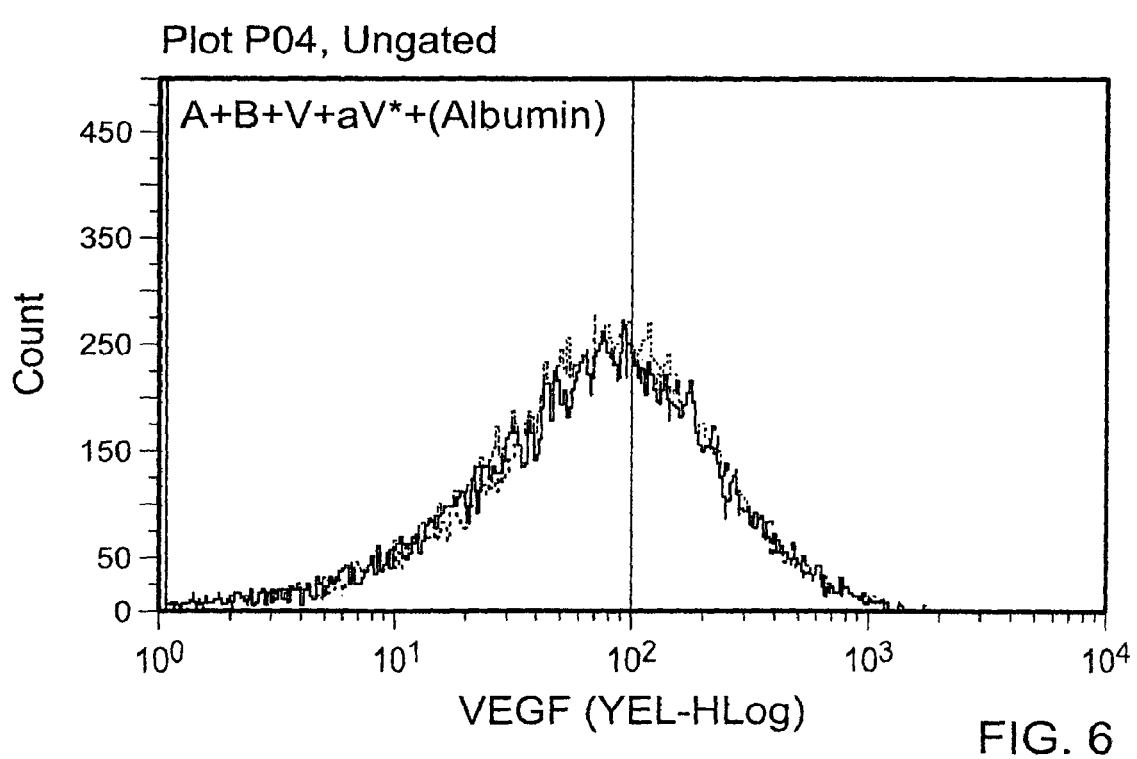
FIG. 6 is a graph plotting flow cytometry data of A plus B incubated in the presence of various concentrations of human serum albumin (500 µg, 50 µg, 5 µg, 0.5 µg, and 0.05 µg/mL) followed by addition of V and aV*. These results indicate that incubation with serum albumin (concentrations ranging from 500 µg/mL to 0.05 µg/mL) did not affect the complexing of A and B.
Figure 7:
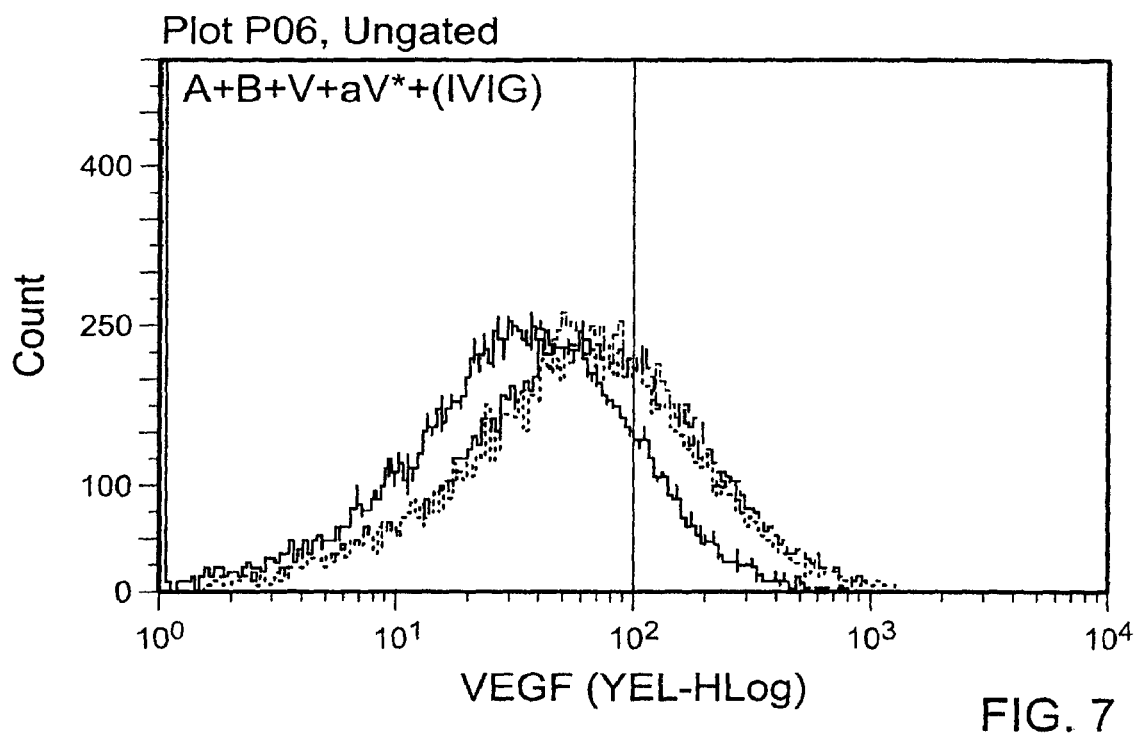
FIG. 7 is a graph plotting flow cytometry data of A plus B incubated in the presence of various concentrations of human polyclonal immunoglobulin (500 µg, 50 µg, 5 µg, 0.5 µg, and 0.05 µg/mL) followed by addition of V and aV*. These results indicate that incubation of A and B with a range of concentrations of human immunoglobulin (IVIG; 500 µg/mL to 0.05 µg/mL) partially inhibited A and B complexing.
Figure 8:
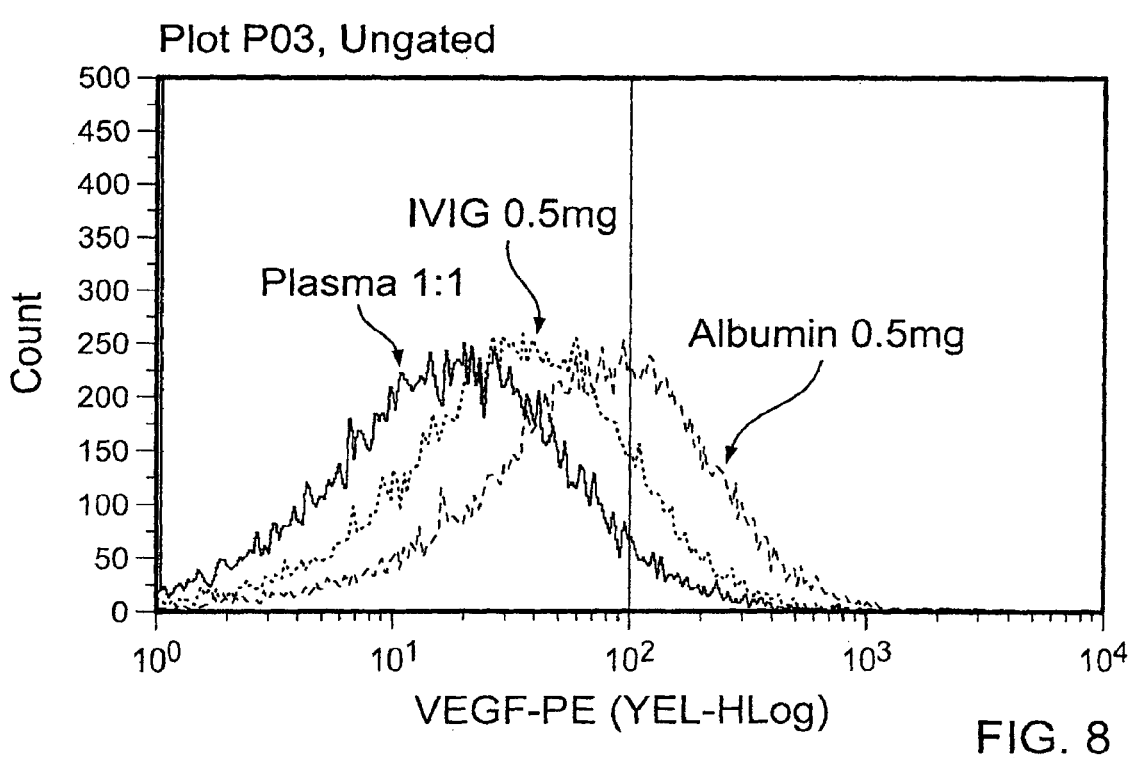
FIG. 8 contain A plus B complexing results in the presence of plasma (1:1), IVIG (0.5 mg/mL), or albumin (0.5 mg/mL). At the highest concentrations of plasma (1:1), IVIG (0.5 mg/mL), or albumin (0.5 mg/mL) tested, the levels of relative inhibition of A plus B complexing differ in diminishing order.

This document provides methods and materials involved in treating cancer (e.g., skin cancers such as melanoma). For example, this document provides methods and materials for using complexes containing albumin-containing nanoparticles (e.g., Abraxane® nanoparticles) and antibodies (e.g., anti-VEGF polypeptide antibodies such as Avastin®) to treat cancer.

The methods and materials provided herein can be used to treat any type of cancer. For example, the methods and materials provided herein can be used to treat skin cancer (e.g., melanoma) and breast cancer. In some cases, the methods and materials provided herein can be used to treat cancer (e.g., skin cancer) in any type of mammal including, without limitation, mice, rats, dogs, cats, horses, cows, pigs, monkeys, and humans. When treating skin cancer, any type of skin cancer, such as melanoma, can be treated using the methods and materials provided herein. For example, stage I, stage II, stage III, or stage IV melanoma can be treated. In some cases, a lymph node positive, a lymph node negative, or a metastatic melanoma can be treated as described herein.

In some cases, complexes containing albumin-containing nanoparticles (e.g., Abraxane® nanoparticles) and antibodies (e.g., anti-VEGF polypeptide antibodies such as Avastin®) can be designed to have an average diameter that is greater than 1 µm. For example, appropriate concentrations of albumin-containing nanoparticles and antibodies can be used such that complexes having an average diameter that is greater than 1 µm are formed. In some cases, manipulations such as centrifugation can be used to form preparations of albumin-containing nanoparticle/antibody complexes where the average diameter of those complexes is greater than 1 µm. In some cases, the preparations of albumin-containing nanoparticle/antibody complexes provided herein can have an average diameter that is between 1 µM and 5 µm (e.g., between 1.1 µm and 5 µm, between 1.5 µm and 5 µm, between 2 µm and 5 µm, between 2.5 µm and 5 µm, between 3 µm and 5 µm, between 3.5 µm and 5 µm, between 4 µm and 5 µm, between 4.5 µm and 5 µm, between 1.1 µm and 4.5 µm, between 1.1 µm and 4 µm, between 1.1 µm and 3.5 µm, between 1.1 µm and 3 µm, between 1.1 µm and 2.5 µm, between 1.1 µm and 2 µm, or between 1.1 µm and 1.5 µm). Preparations of albumin-containing nanoparticle/antibody complexes provided herein having an average diameter that is between 1 µm and 5 µm can be administered systemically (e.g., intravenously) to treat cancers located within a mammal's body. In some cases, the preparations of albumin-containing nanoparticle/antibody complexes provided herein can have an average diameter that is between 5 µm and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 µm, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparations of albumin-containing nanoparticle/antibody complexes provided herein having an average diameter that is between 5 µm and 50 µm can be administered into a tumor (e.g., intratumorally) or in a region of a tumor located within a mammal's body.

In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 1 µm and 5 µm (e.g., between 1.1 µm and 5 µm, between 1.5 µm and 5 µm, between 2 µm and 5 µm, between 2.5 µm and 5 µm, between 3 µm and 5 µm, between 3.5 µm and 5 µm, between 4 µm and 5 µm, between 4.5 µm and 5 µm, between 1.1 µm and 4.5 µm, between 1.1 µm and 4 µm, between 1.1 µm and 3.5 µm, between 1.1 µm and 3 µm, between 1.1 µm and 2.5 µm, between 1.1 µm and 2 µm, or between 1.1 µm and 1.5 µm). Preparation of albumin-containing nanoparticle/antibody complexes provided herein having greater than 60 percent (e.g., greater than 65, 70, 75, 80, 90, 95, or 99 percent) of the complexes with a diameter that is between 1 µm and 5 µm can be administered systemically (e.g., intravenously) to treat cancers located within a mammal's body. In some cases, a preparation of albumin-containing nanoparticle/antibody complexes provided herein can have greater than 60 percent (e.g., greater than 65, 70, 75, 80, 90, 95, or 99 percent) of the complexes having a diameter that is between 5 µm and 50 µm (e.g., between 6 µm and 50 µm, between 7 µm and 50 µm, between 10 µm and 50 µm, between 15 µm and 50 µm, between 20 µm and 50 µm, between 25 µm and 50 µm, between 30 µm and 50 µm, between 35 µm and 50 µm, between 5 µm and 45 µm, between 5 µm and 40 µm, between 5 µm and 35 µm, between 5 µm and 30 µm, between 5 µm and 25 µm, between 5 µm and 20 µm, between 5 µm and 15 µm, or between 10 µm and 30 µm). Preparation of albumin-containing nanoparticle/antibody complexes provided herein having greater than 60 percent (e.g., greater than 65, 70, 75, 80, 90, 95, or 99 percent) of the complexes with a diameter that is between 5 µm and 50 µm can be administered into a tumor (e.g., intratumorally) or in a region of a tumor located within a mammal's body.

In general, albumin-containing nanoparticles such as Abraxane® can be contacted with an antibody such as an anti-VEGF polypeptide antibody (e.g., Avastin®) prior to administration to a human to form an albumin-containing nanoparticle/antibody complex (e.g., an Abraxane®/anti-VEGF polypeptide antibody complex). Any appropriate albumin-containing nanoparticle preparation and any appropriate antibody can be used as described herein. For example, Abraxane® nanoparticles can be used as described herein. Examples of antibodies that can be used to form albumin-containing nanoparticle/antibody complexes as described herein include, without limitation, bevacizumab (Avastin®), trastuzumab, and rituxan. For example, an appropriate dose of Abraxane® and an appropriate dose of Avastin® can be mixed together in the same container. This mixture can be incubated at an appropriate temperature (e.g., room temperature, between 15° C. and 30° C., between 15° C. and 25° C., between 20° C. and 30° C., or between 20° C. and 25° C.) for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 400 minutes, or between about 25 minutes and about 35 minutes) before being administered to a cancer patient (e.g., a melanoma patient). In some cases, Abraxane® can be contacted with an anti-VEGF polypeptide antibody by injecting both Abraxane® and the anti-VEGF polypeptide antibody either individually or as a pre-mixed combination into an IV bag containing an IV bag solution. The contents of the IV bag including Abraxane®/anti-VEGF polypeptide antibody complexes can be introduced into the patient to be treated.

In some cases, albumin-containing nanoparticles such as Abraxane® can be contacted with an antibody such as an anti-VEGF polypeptide antibody (e.g., Avastin®) to form albumin-containing nanoparticle/antibody complexes (e.g., Abraxane®/anti-VEGF polypeptide antibody complexes) that are stored prior to being administered to a cancer patient (e.g., a melanoma patient). For example, a composition containing albumin-containing nanoparticle/antibody complexes can be formed as described herein and stored for a period of time (e.g., days or weeks) prior to being administered to a cancer patient.

Any appropriate method can be used to obtain albumin-containing nanoparticles such as Abraxane® and an antibody such as an anti-VEGF polypeptide antibody. For example, Abraxane® can be obtained from Celgene Corp. or as described elsewhere (U.S. Pat. No. 6,537,579). Avastin® can be obtained from Genentech Corp. or Roche Corp. or as described elsewhere (U.S. Pat. No. 6,054,297).

In some cases, the combination of an albumin-containing nanoparticle such as Abraxane® and an antibody such as anti-VEGF polypeptide antibody can include one or more other agents such as an alkylating agent (e.g., a platinum compound). Examples of platinum compounds that can be used as an alkylating agent include, without limitation, carboplatin (Paraplatin®), cisplatin (Platinol®), oxaliplatin (Eloxatin®), and BBR3464. Examples of other agents that can be included within an albumin-containing nanoparticle/antibody complex provided herein include, without limitation, bendamustine, bortezomib, cabazitaxel, chlorambucil, dasatinib, docetaxel, doxorubicin, epirubicin, erlotinib, etoposide, everolimus, gefitinib, idarubicin, hydroxyurea, imatinib, lapatinib, melphalan, mitoxantrone, nilotinib, oxaliplatin, pazopanib, pemetrexed, romidepsin, sorafenib, sunitinib, teniposide, vinblastine, and vinorelbine.

Any appropriate method can be used to administer an albumin-containing nanoparticle/antibody complex provided herein (e.g., Abraxane®/anti-VEGF polypeptide antibody complexes) to a mammal. For example, a composition containing albumin-containing nanoparticle/antibody complexes such as Abraxane®/anti-VEGF polypeptide antibody complexes can be administered via injection (e.g., subcutaneous injection, intramuscular injection, intravenous injection, or intrathecal injection).

Before administering a composition containing an albumin-containing nanoparticle/antibody complex provided herein (e.g., Abraxane®/anti-VEGF polypeptide antibody complexes) to a mammal, the mammal can be assessed to determine whether or not the mammal has cancer (e.g., skin cancer). Any appropriate method can be used to determine whether or not a mammal has cancer (e.g., skin cancer). For example, a mammal (e.g., human) can be identified as having skin cancer using standard diagnostic techniques. In some cases, a tissue biopsy can be collected and analyzed to determine whether or not a mammal has skin cancer.

After identifying a mammal as having cancer (e.g., skin cancer), the mammal can be administered a composition containing albumin-containing nanoparticle/antibody complexes provided herein (e.g., Abraxane®/anti-VEGF polypeptide antibody complexes). For example, a composition containing Abraxane®/anti-VEGF polypeptide antibody complexes can be administered prior to or in lieu of surgical resection of a tumor. In some cases, a composition containing albumin-containing nanoparticle/antibody complexes provided herein (e.g., Abraxane®/anti-VEGF polypeptide antibody complexes) can be administered following resection of a tumor.

A composition containing albumin-containing nanoparticle/antibody complexes provided herein (e.g., Abraxane®/anti-VEGF polypeptide antibody complexes) can be administered to a mammal in any appropriate amount, at any appropriate frequency, and for any appropriate duration effective to achieve a desired outcome (e.g., to increase progression-free survival). In some cases, a composition containing albumin-containing nanoparticle/antibody complexes provided herein (e.g., Abraxane®/anti-VEGF polypeptide antibody complexes) can be administered to a mammal having cancer (e.g., skin cancer) to reduce the progression rate of the cancer (e.g., melanoma) by 5, 10, 25, 50, 75, 100, or more percent. For example, the progression rate can be reduced such that no additional cancer progression is detected. Any appropriate method can be used to determine whether or not the progression rate of cancer (e.g., skin cancer) is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer (e.g., skin cancer) after treatment can be determined and compared to the stage before treatment to determine whether or not the progression rate was reduced.

In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where progression-free survival is increased (e.g., by 5, 10, 25, 50, 75, 100, or more percent) as compared to the median progression-free survival of corresponding mammals having untreated cancer (e.g., untreated skin cancer) or the median progression-free survival of corresponding mammals having cancer (e.g., skin cancer) treated with Abraxane® and an antibody (e.g., an anti-VEGF polypeptide antibody) without forming Abraxane®/antibody complexes (e.g., without forming Abraxane®/anti-VEGF polypeptide antibody complexes). In some cases, a composition containing albumin-containing nanoparticle/antibody complexes provided herein (e.g., Abraxane®/anti-VEGF polypeptide antibody complexes) can be administered to a mammal having cancer (e.g., skin cancer) to increase progression-free survival by 5, 10, 25, 50, 75, 100, or more percent as compared to the median progression-free survival of corresponding mammals having cancer (e.g., skin cancer) and having received Abraxane® or an antibody (e.g., an anti-VEGF polypeptide antibody) alone. Progression-free survival can be measured over any length of time (e.g., one month, two months, three months, four months, five months, six months, or longer).

In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing albumin-containing nanoparticle/antibody complexes provided herein (e.g., Abraxane®/anti-VEGF polypeptide antibody complexes). In some cases, a composition containing albumin-containing nanoparticle/antibody complexes provided herein (e.g., Abraxane®/anti-VEGF polypeptide antibody complexes) can be administered to a mammal having cancer (e.g., skin cancer) under conditions where the median time to progression for a population of mammals is at least 150 days (e.g., at least 155, 160, 163, 165, or 170 days).

An effective amount of a composition containing albumin-containing nanoparticle/antibody complexes provided herein (e.g., Abraxane®/anti-VEGF polypeptide antibody complexes) can be any amount that reduces the progression rate of cancer (e.g., skin cancer), increases the progression-free survival rate, or increases the median time to progression without producing significant toxicity to the mammal. Typically, an effective amount of Abraxane® can be from about 50 mg/m$^2$ to about 150 mg/m$^2$ (e.g., about 80 mg/m$^2$), and an effective amount of an anti-VEGF polypeptide antibody such as bevacizumab can be from about 5 mg/kg to about 20 mg/kg (e.g., about 10 mg/kg). If a particular mammal fails to respond to a particular amount, then the amount of Abraxane® or anti-VEGF polypeptide antibody can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., skin cancer) may require an increase or decrease in the actual effective amount administered.

The frequency of administration can be any frequency that reduces the progression rate of cancer (e.g., skin cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing Abraxane®/anti-VEGF polypeptide antibody complexes can include rest periods. For example, a composition containing Abraxane®/anti-VEGF polypeptide antibody complexes can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the skin cancer may require an increase or decrease in administration frequency.

An effective duration for administering a composition provided herein can be any duration that reduces the progression rate of cancer (e.g., skin cancer), increases the progression-free survival rate, or increases the median time to progression without producing significant toxicity to the mammal. Thus, the effective duration can vary from several days to several weeks, months, or years. In general, the effective duration for the treatment of skin cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., skin cancer).

A composition containing albumin-containing nanoparticle/antibody complexes provided herein (e.g., Abraxane®/anti-VEGF polypeptide antibody complexes) can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the cancer (e.g., skin cancer) was treated. For example, a mammal can be assessed after treatment to determine whether or not the progression rate of melanoma was reduced (e.g., stopped). As described herein, any method can be used to assess progression and survival rates.

In some cases, nanoparticles containing albumin (e.g., nanoparticles with an albumin shell) and an agent other than placitaxel can be used as described herein in place of or in combination with Abraxane®. For example, albumin-containing nanoparticles designed to carry a cancer chemotherapeutic agent can be used to form nanoparticle/anti-VEGF polypeptide antibody complexes that can be used as described herein. An example of such a cancer chemotherapeutic agent includes, without limitation, vinblastine.

The invention will be further described in the following examples, which do not limit the scope of the invention described in the claims.

EXAMPLES

Example 1—Contacting Abraxane® with Avastin® Results in the Formation of Abraxane®/Avastin® Complexes Abraxane® (1 mg/mL) and Avastin (25 mg/mL) were stored at 4° C. 10 µg (10 µL) of Abraxane® nanoparticles and 500 µg (20 µL) of Avastin were mixed in a total volume of 30 µL. The Abraxane® and Avastin were incubated at room temperature for 30 minutes.

After incubation, the Abraxane® nanoparticles were spun and washed three times with 1×PBS to eliminate unbound bevacizumab. The nanoparticles were spun at 5000 rpm for 5 minutes and resuspended in 50 µL of 1×PBS.

100 ng or 500 ng of VEGF was added to each tube for 30 minutes at room temperature, and the washes were repeated to eliminate unbound VEGF. PE anti-human VEGF was added at a 1:50 dilution, and the particles were once again incubated and washed. Visualization was done by flow cytometry, and percentage of PE (VEGF) positive particles was determined (FIGS. 1-4). Various combinations of agents were tested as indicated in the figures. These results demonstrate that Abraxane® and bevacizumab spontaneously associate in a manner that preserves VEGF binding potential.

Figure 9:
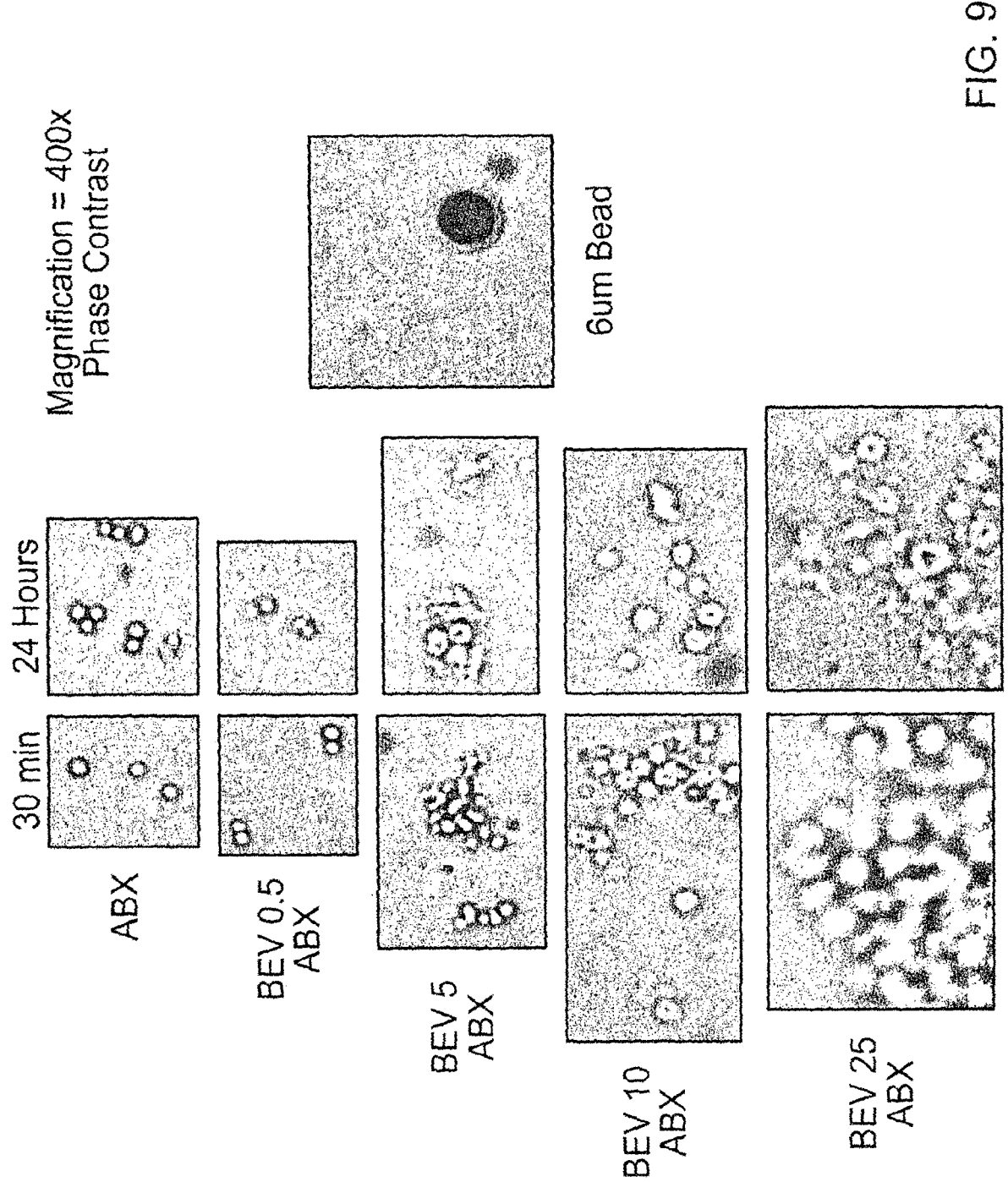
FIG. 9 contains photographs of light microscope images of Abraxane® (ABX) or mixtures of Abraxane® (ABX) and bevacizumab (BEV; 0.5, 5, 10, or 25 mg/mL) either 4 or 24 hours after mixing.

Abraxane® nanoparticles were mixed with varying concentrations of bevacizumab (0.5, 5, 10, and 25 mg/mL). The particles were viewed by light microscopy at 4 and 24 hours after mixing. The macromolecular size of the ABX:BEV complexes was dependent on the concentration of the bevacizumab added and the Abraxane® nanoparticles (FIG. 9). Once a maximum size was reached, the ABX:BEV complexes began to break down within about 24 hours (FIG. 9).

Figure 10:
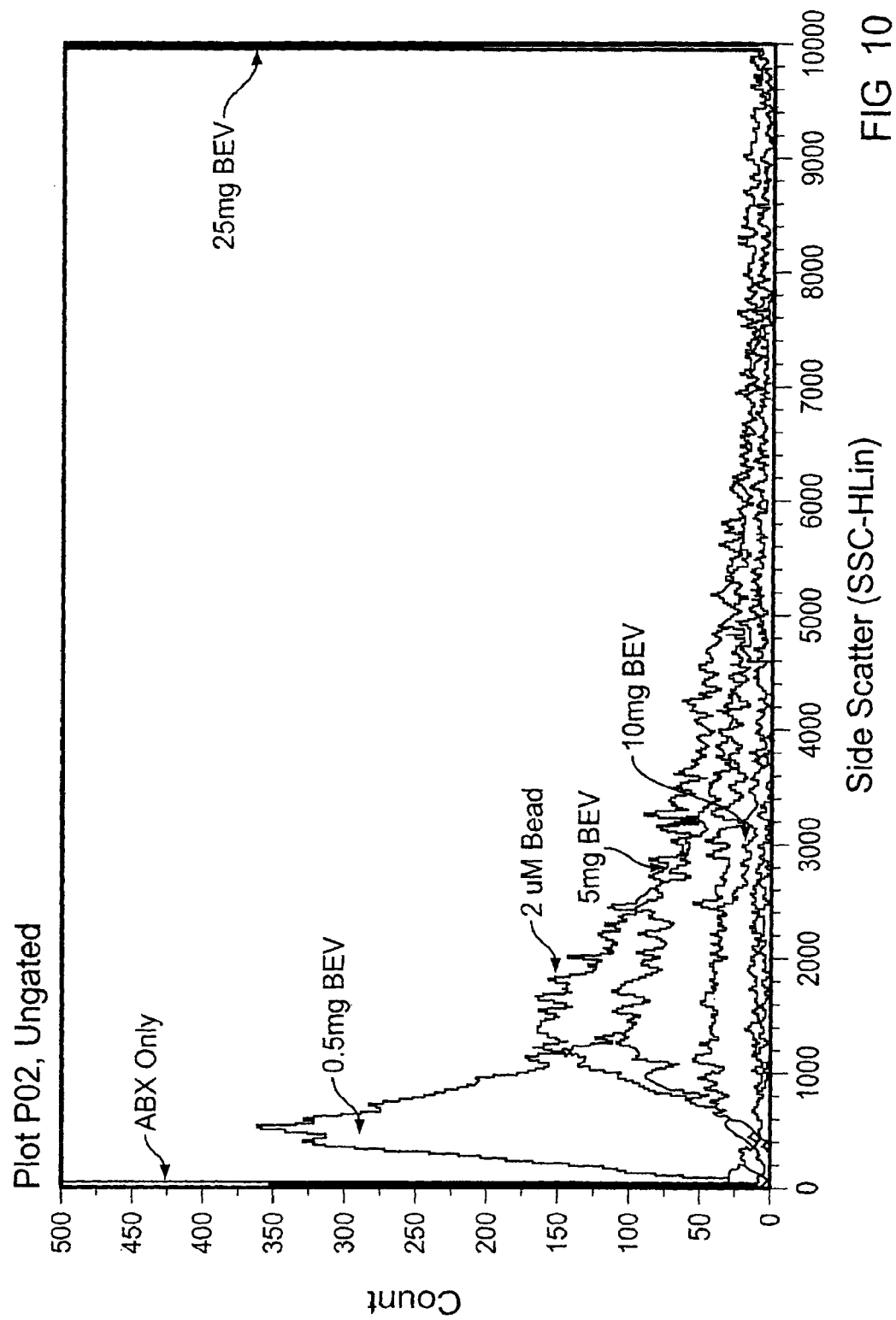
FIG. 10 is a graph plotting flow cytometry results of Abraxane® alone, ABX:BEV complexes, and 2 µm standard beads.

Bevacizumab was added to Abraxane® nanoparticles in varying concentrations (0.5, 5, 10, 25 mg/mL) and incubated for 30 minutes at room temperature to allow complex formation. Abraxane® nanoparticles alone, ABX:BEV complexes, and 2 µm standard beads were visualized by flow cytometry. The complex size increased with increased concentrations of bevacizumab (FIG. 10). The larger the particle-size, the further to the right the peak will be. These results demonstrate that complex size can be manipulated by varying the concentration of bevacizumab added.

In another study, Abraxane® nanoparticles and bevacizumab were incubated together for 4 hours and overnight at 1 mg/mL or 10 mg/mL. Abraxane® nanoparticles alone were also incubated for 4 hours and overnight as a control. After the allotted time was reached, the complexes were spun down at 7500 RPM for 5 minutes. The supernatants were collected and mixed 1:1 with Laemmli buffer and boiled at 100 degrees for 3 minutes. 20 µL of sample was loaded onto a 7.5% Tris-HCl Criteron gel. A high range molecular weight marker (BioRad) was added for size determination. The gel was run for 3 hours at 75V.

After the gel ran to completion, the gel was placed in a transfer cassette so the proteins could be moved onto a PVDF membrane. The transfer took place overnight at 4° C. running at 20V. The membrane was removed and rocked in TBST containing 5% milk to block for 3 hours at room temperature. The primary antibodies used were Rabbit anti- Taxol (1:500 dilution) and goat anti-mouse IgG-Fab specific-HRP conjugated (1:500 dilution). Antibodies were diluted into 10 mL of TBST with 5% milk. Primary antibodies were allowed to bind overnight at 4° C. while rocking.

Primary antibodies were removed, and the membranes were washed three times for 10 minutes with TBST. The taxol blot was incubated in a 1:1000 dilution of secondary anti-rabbit IgG-HRP for 1.5 hours rocking at room temperature. The anti-mouse IgG (Bevacizumab) membrane was incubated in ECL detection reagent (GE Amershem) for 5 minutes before it was exposed to film. Membrane was exposed for 10 seconds, 1 minute, and 5 minutes.

After the incubation in secondary antibody, the taxol blot was washed with TBST for 10 minutes three times. The membrane was then placed in ECL detection reagent for 5 minutes and exposed to film. The exposure times were 1 second, 2 seconds, and 10 seconds.

Figure 14:
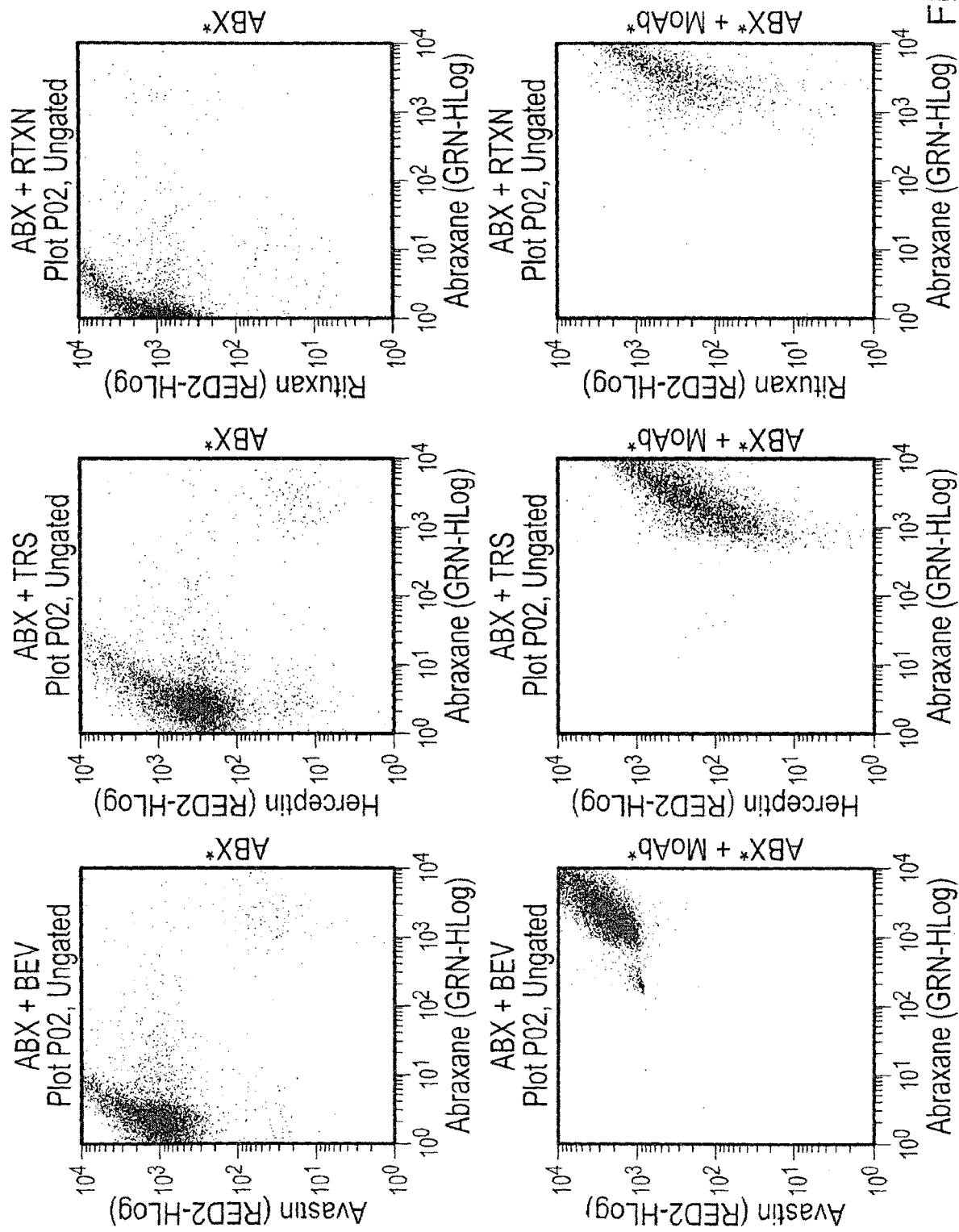
FIG. 14 contains scatter plots of a flow cytometry analysis of the indicated complexes containing Abraxane®.
Figures 14, 15:
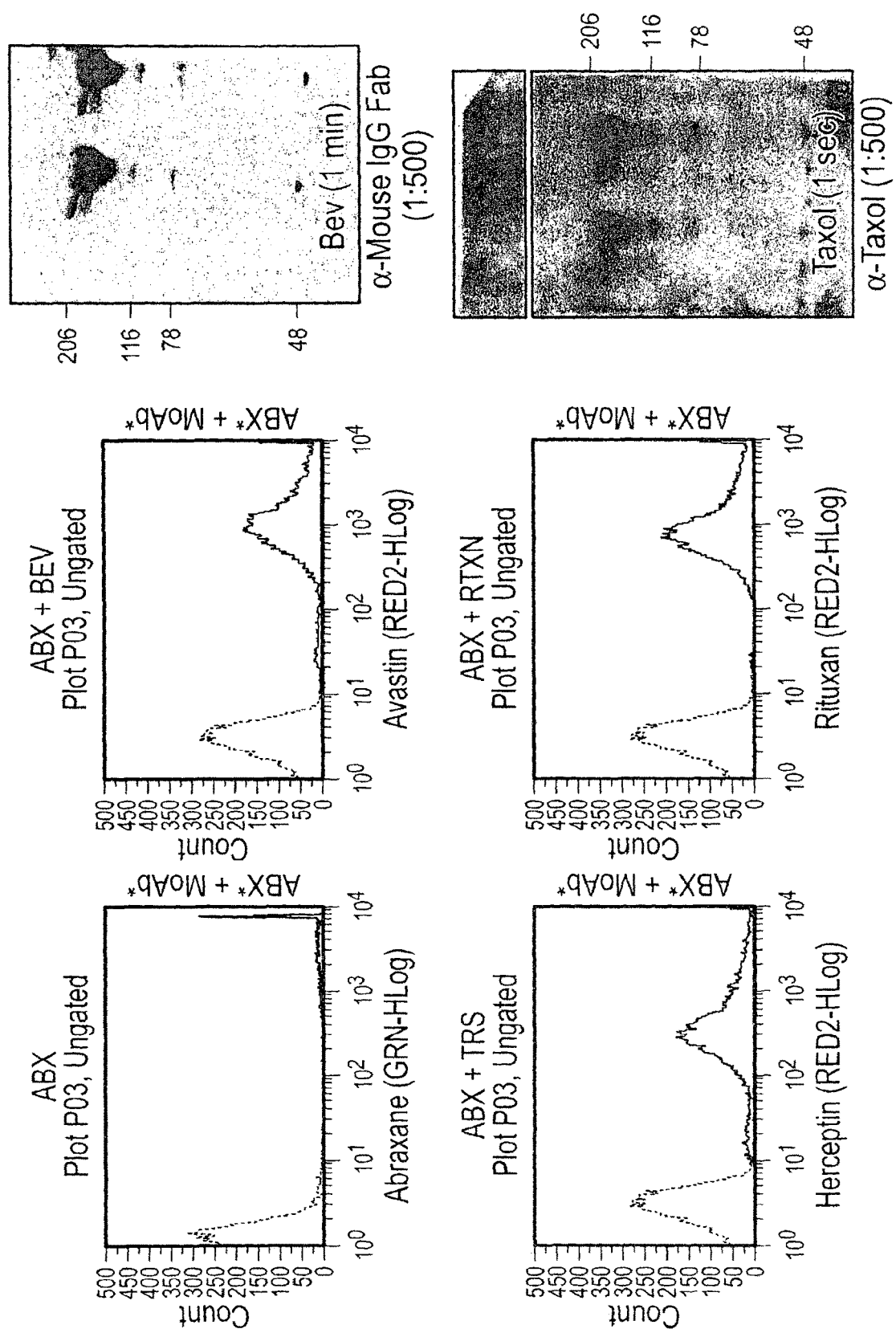
FIG. 15 contains photographs of Western blot analyses of the indicated materials assessed for bevacizumab or taxol.

The IgG blot was specific for the mouse portion of the bevacizumab humanized antibody. A clear concentration dependent increase from complexes mixed at 1 mg/mL to 10 mg/mL was observed (FIG. 15). Taxol is a small molecule around 20 kDa. Free taxol was observed at the bottom of the blot, but it also was observed running at the bevacizumab molecular weight (149 kDa; FIG. 15). These results demonstrate that taxol was bound to the bevacizumab in the supernatant after the large particles were removed by centrifugation.

Figure 16:
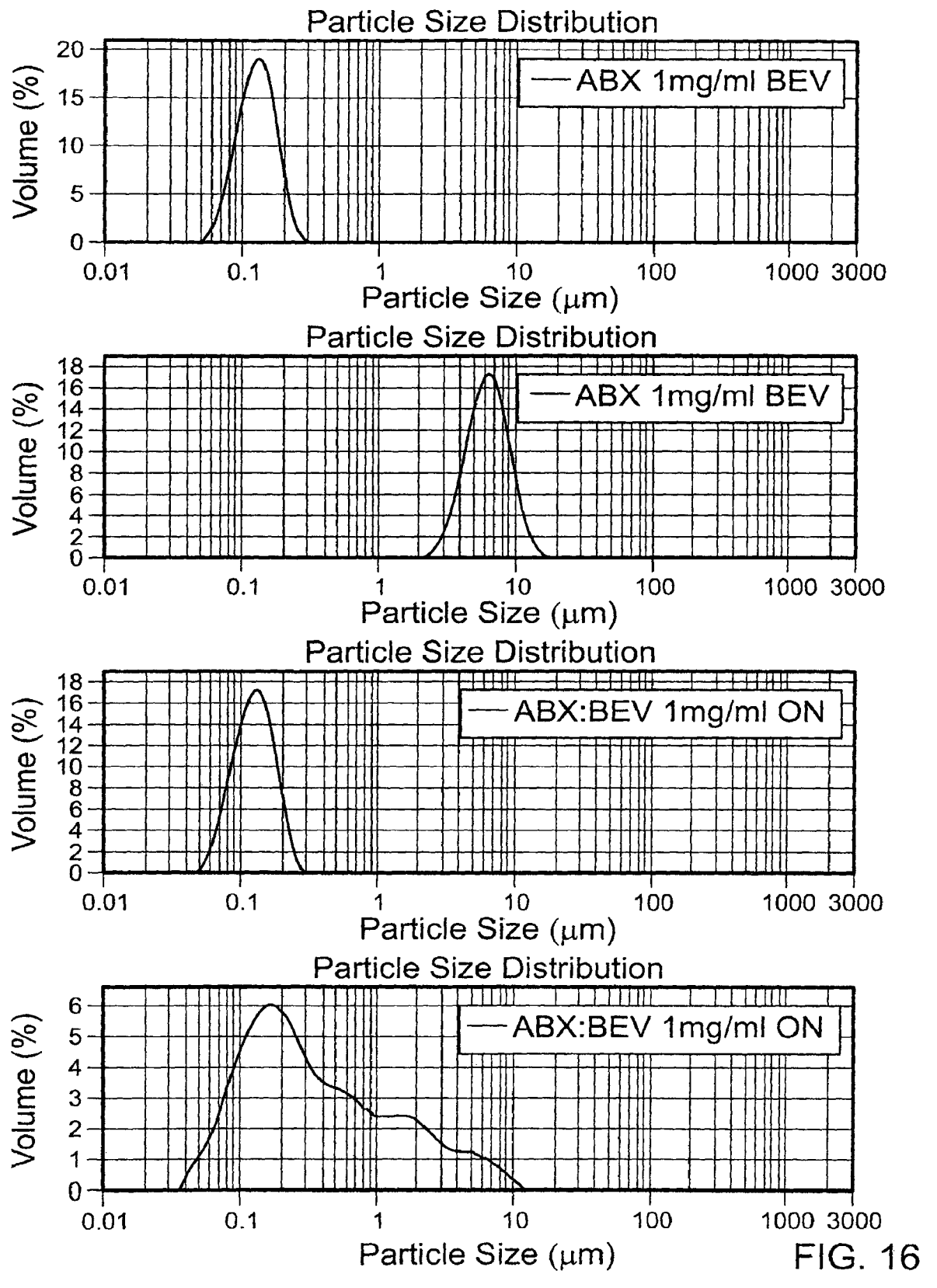
Figure 17:
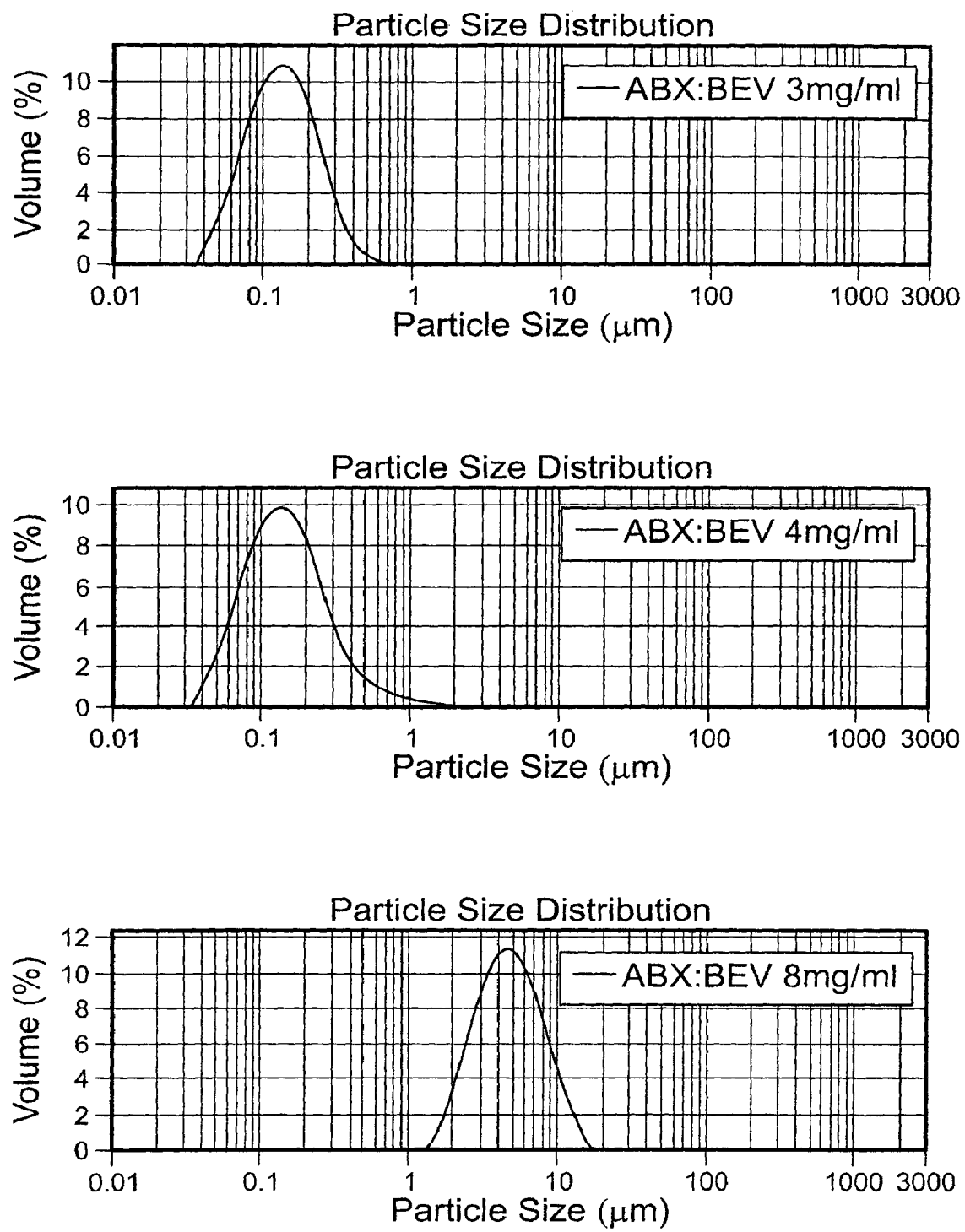
FIG. 17 contains graphs of the size distributions of the indicated complexes incubated for one hour at room temperature.

In another study, Abraxane® nanoparticles and bevacizumab were incubated for various times (1, 4, and 12 hours), and the particle size distribution of the resulting complexes was determined relative to Abraxane® nanoparticles alone using the Malvern Mastersizer 2000E. The size of the complexes generated was a function of antibody concentration and incubation time (FIGS. 16 and 17). In FIGS. 16, 1 and 10 mg/mL of bevacizumab was incubated with Abraxane® nanoparticles for 4 hours and overnight. The complexes generated with 10 mg/mL bevacizumab were much larger (8.479 μm) than those with 1 mg/mL bevacizumab (0.165 μm). After an overnight incubation, the larger complexes began to break down.

In FIG. 17, complex size increased with concentration of bevacizumab added when incubated for 1 hour at room temperature. In addition, larger complexes were formed when 1 mg/mL bevacizumab was incubated with Abraxane® nanoparticles, spun, and resuspended as compared to the size observed when the same amount (1 mg/mL) of bevacizumab was incubated with Abraxane® nanoparticles without spinning the preparation (FIG. 17). These results demonstrate that complex size can be manipulated by altering concentrations, by manual forces (e.g., centrifugation), or by both.

Figure 20:
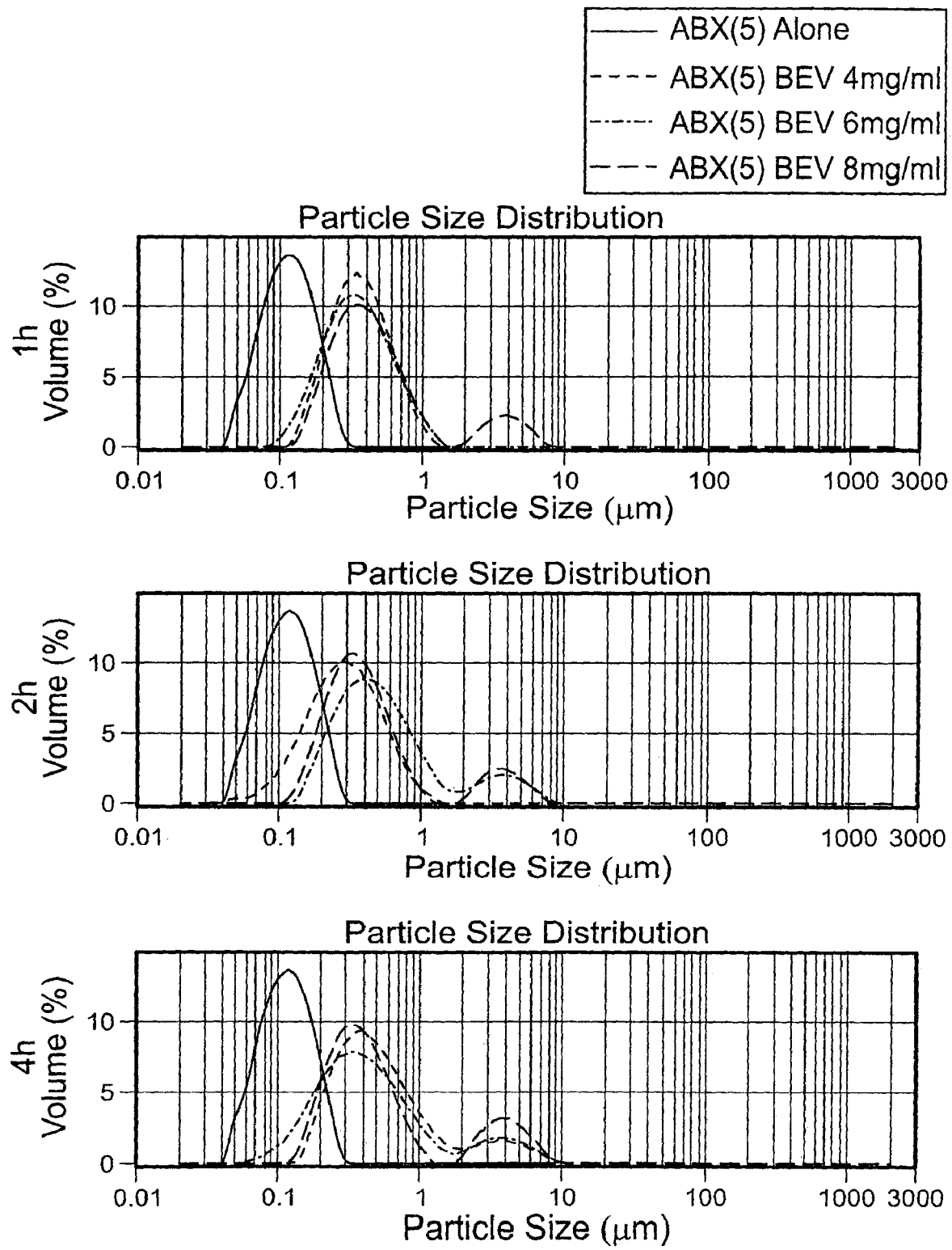
FIG. 20 contains graphs plotting the particle size distribution for ABX:BEV complexes as determined using a Mastersizer 2000E (Malvern Instruments Ltd., Worcestershire, England). ABX (20 mg/mL) and BEV (16, 24, or 32 mg/mL) were incubated for 1, 2, or 4 hours at room temperature. After incubation, the mixtures were diluted 1:4 for a final concentration of ABX (5 mg/mL) and BEV (4, 6, or 8 mg/mL), and the diluted samples analyzed using a Mastersizer 2000E.

In another study, Abraxane® nanoparticles were dissolved at a concentration of 20 mg/mL, and bevacizumab was added at a final concentration of 16, 24, or 32 mg/mL. The mixtures were incubated at room temperature for various times (1, 2, and 4 hours). After this incubation, the mixture was diluted 1:4 (final concentration of Abraxane=5 mg/mL; final concentrations of bevacizumab=4, 6, or 8 mg/mL). The particle size distribution of the resulting complexes was determined relative to Abraxane® nanoparticles alone using the Malvern Mastersizer 2000E. The size of the complexes generated was a function of antibody concentration and incubation time (FIG. 20).

Abraxane and bevacizumab were mixed and incubated for 30 minutes at room temperature to allow complex formation. Mice were injected with 100 μL of the complexes containing 5 mg of Abraxane and 1 mg of bevacizumab in the dorsal tail vein. Injection of the complexes did not harm any mice.

Example 2—Human Plasma Inhibits the Formation of Abraxane®/Avastin® Complexes

10 μL (10 μg) of Abraxane® was added to eppendorf tubes, and 500 μg (25 μL) of avastin was added and resuspended in a final volume of 50 μL. Human plasma was titrated using 1:2 dilutions (1:2, 1:4, 1:8, or 1:16). 50 μL of plasma and 50 μL of each plasma titration were added to the tubes with Abraxane® and avastin. In some cases, human serum albumin (500 μg, 50 μg, 5 μg, 0.5 μg, or 0.05 μg/mL) or human polyclonal immunoglobulin (500 μg, 50 μg, 5 μg, 0.5 μg, and 0.05 μg/mL) was added to the tubes in place of human plasma.

After a 30 minute incubation at room temperature, the Abraxane® nanoparticles were washed in 1×PBS twice. 100 ng of VEGF was added to each tube for 30 minutes at room temperature, and the washes were repeated. PE anti-human VEGF was added at a 1:50 dilution, and particles were once again incubated and washed. Visualization was done by flow cytometry, and percentage of PE (VEGF) positive particles was determined (FIG. 5-8).

Figure 11:
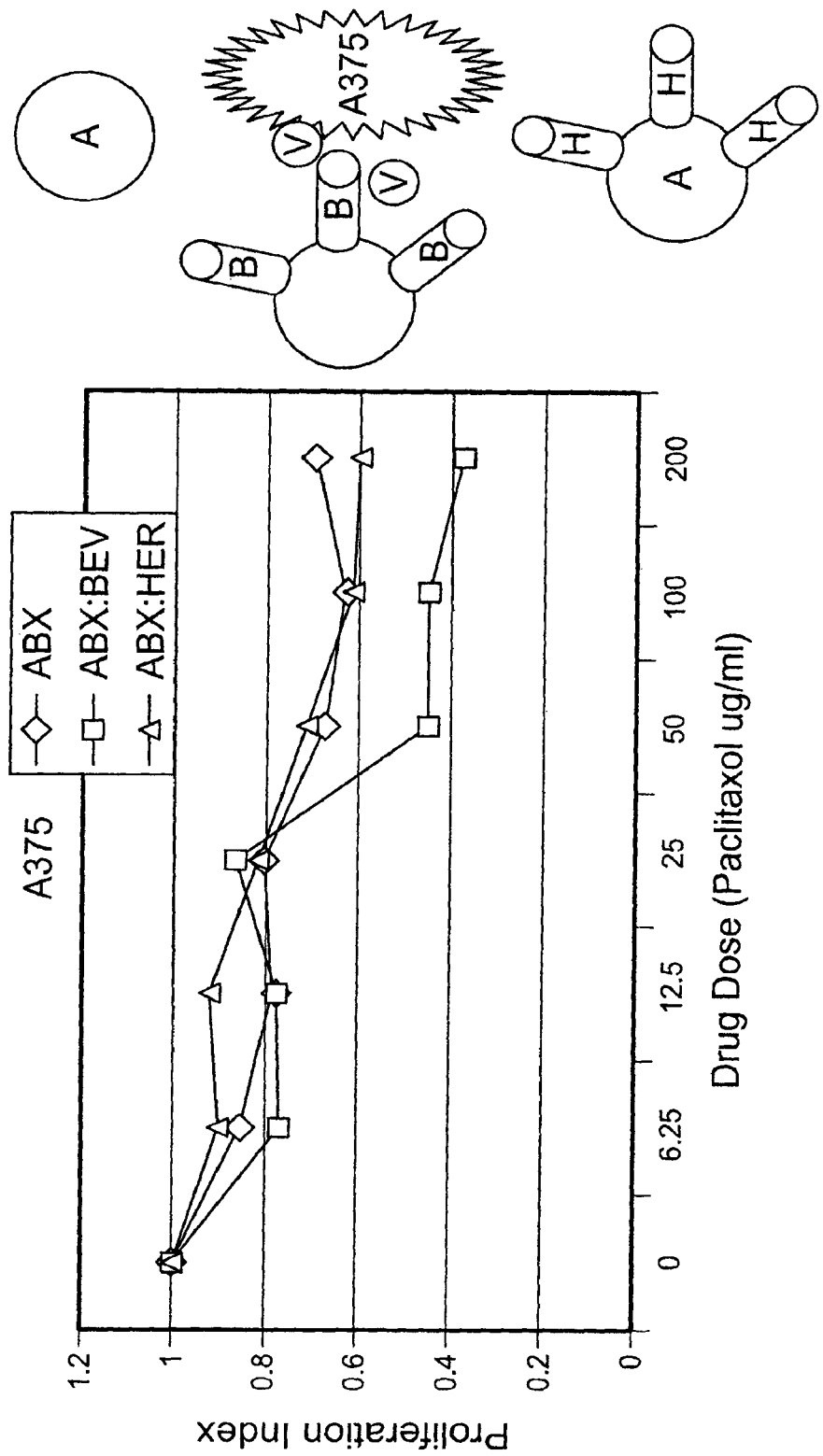
FIG. 11 is graph plotting the proliferation index for A375 cells (a melanoma tumor cell line) exposed to Abraxane® (ABX) only, Abraxane®:Herceptin (non-VEGF targeting) complexes, or Abraxane®:Bevacizumab (VEGF targeting) complexes at the indicated dose.

Example 3—Abraxane®/Avastin® Complexes have a Higher Level of Cell Toxicity than Abraxane® Alone or Abraxane®/Herceptin Complexes The VEGF producing melanoma tumor cell line, A375, was incubated overnight in the presence of Abraxane® nanoparticles only, Abraxane®/Herceptin (non-VEGF targeting) complexes, and Abraxane®/Avastin® (ABX:BEV; VEGF targeting) complexes. Increasing doses of drug were added to the cells to give 6.25, 12.5, 25, 50, 100, and 200 μg/mL of taxol. After the overnight incubation, cell proliferation was determined by measuring the level of DNA synthesis. A higher level of cell toxicity (less DNA synthesis) of cells incubated with the VEGF targeting complexes (ABX:BEV) relative the ABX alone and non-VEGF targeted complexes (ABX:HER) (FIG. 11).

Example 4—Stability of Abraxane®/Avastin® Complexes

Figure 12:
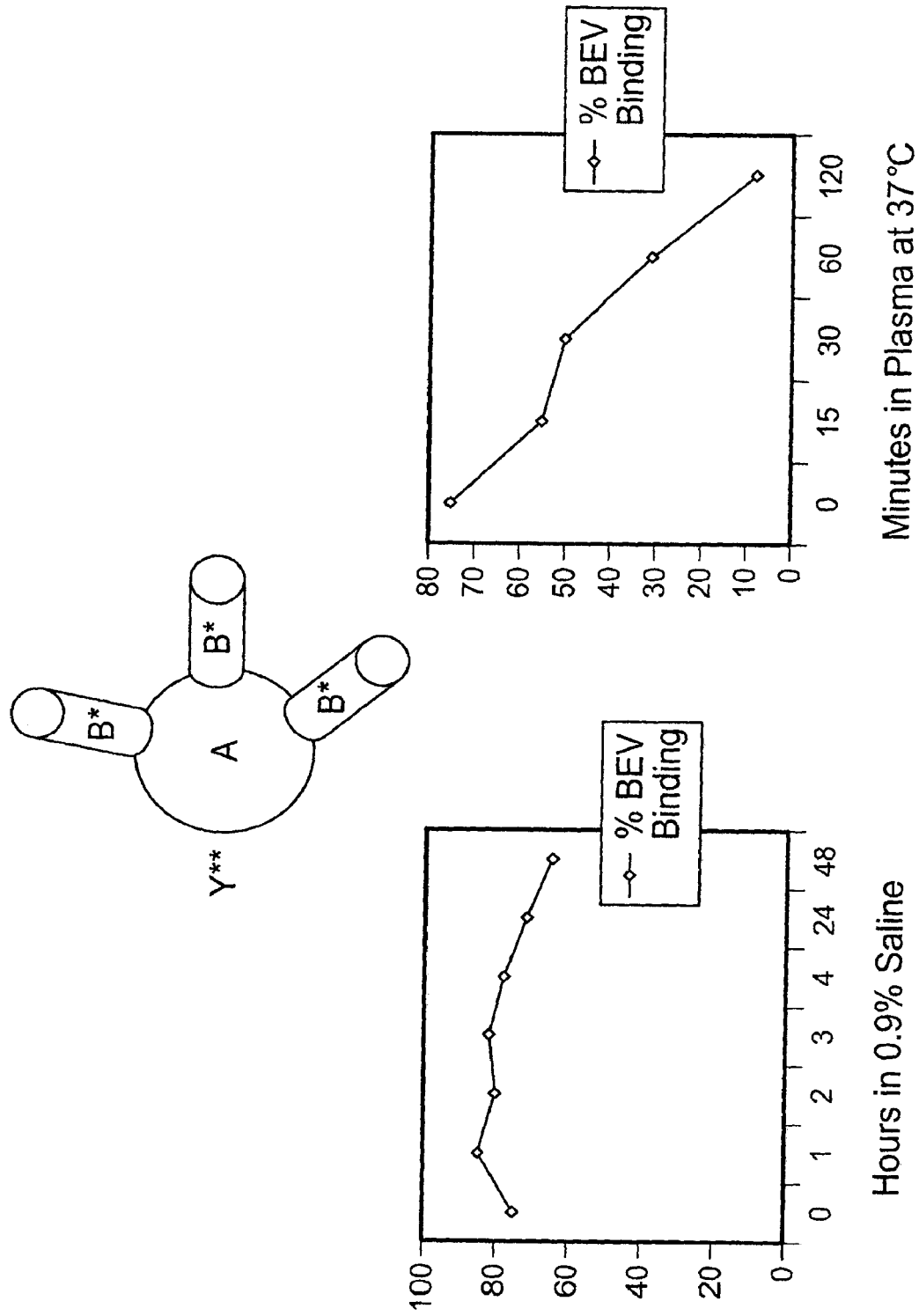
FIG. 12 contains graphs plotting the percent BEV binding for ABX:BEV complexes exposed to 0.9% saline at room temperature or human plasma at 37° C. for the indicated times.

Abraxane®/Avastin® complexes were fluorescently labeled such that both the albumin of the Abraxane® and the bevacizumab were directly labeled with a fluorescent marker. The complexes were visualized by flow cytometry after 0, 1, 2, 3, 4, 24, and 48 hours in 0.9% saline at room temperature and after 0, 15, 30, 60, and 120 minutes in human plasma at 37° C. The complexes were stable in saline at room temperature with only about 10% loss at 24 hours (FIG. 12). In human plasma at 37° C., the complexes began to break down in about 15 minutes and were completely undetectable by 120 minutes.

Example 5—Abraxane®/Cisplatin Complexes

Figure 13:
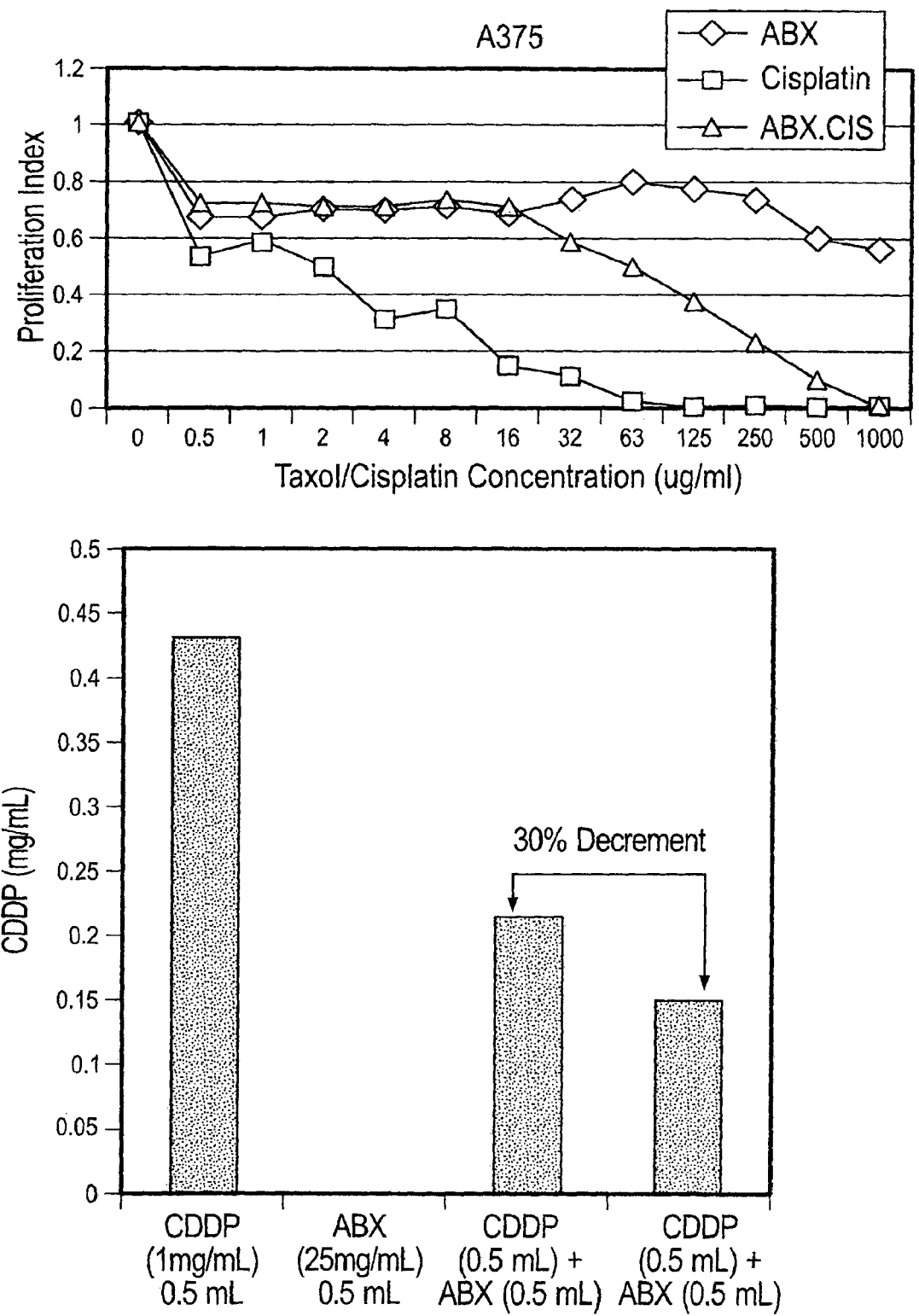
FIG. 13 contains a line graph plotting the proliferation index for A375 cells exposed to Abraxane® (ABX) only, cisplatin only, or Abraxane®:cisplatin complexes at the indicated dose and contains a bar graph plotting demonstrating that 30% of cisplatin (CDDP) remained unbound after ABX:cisplatin were mixed and incubated for 30 minutes.

Abraxane® nanoparticles were incubated with cisplatin (cisplatinum or cis-diamminedichloroplatinum(II) (CDDP)) for 30 minutes at 37° C. The particles were spun, and the supernatant was tested by HPLC to determine how much free cisplatin was in suspension. Cisplatin spontaneously bound to the Abraxane® nanoparticles, and the amount remaining in suspension after the 30 minute incubation with the Abraxane® nanoparticles was only about 30% of the original concentration (FIG. 13). These results demonstrate that about 70% of the cisplatin bound to the Abraxane® nanoparticles.

In another experiment, Abraxane®/cisplatin complexes were generated as described above and added to A375 tumor cells. After an overnight incubation, proliferation of the cells was measured by determining the level of DNA synthesis. The toxicity of the Abraxane®/cisplatin complexes was measured relative to the two drugs individually. The Abraxane®/cisplatin complexes were more toxic to cells (lower level of DNA synthesis) than Abraxane® alone but less toxic than cisplatin alone (FIG. 13). These results demonstrate that cisplatin can be bound to Abraxane® nanoparticles and delivered to tumors without the highly toxic side effects of cisplatin alone.

Example 6—Abraxane®/Antibody Complexes

Three therapeutic monoclonal antibodies (bevacizumab, trastuzamab, and rituxan) were fluorescently labeled and incubated with fluorescently labeled Abraxane® nanoparticles. The particles were spun down, washed, and visualized by flow cytometry. All three of these recombinant therapeutic antibodies spontaneously formed complexes with Abraxane® nanoparticles (FIG. 14). These results demonstrate that albumin-containing nanoparticles can be used to form larger complexes not only with bevacizumab antibodies but also with other antibodies such as trastuzamab and rituxan.

Taken together, the results provided herein demonstrate that in vitro mixing of albumin-containing nanoparticles (e.g., Abraxane® nanoparticles) and antibodies (e.g., bevacizumab, trastuzamab, or rituxan) leads to macromolecular complex formation, the characteristics of which (e.g., size, antibody content, or chemotherapeutic drug content) can be customized depending on need. These results also demonstrate that the macromolecular complexes retain antibody mediated target binding specificity, retain or exhibit enhanced chemotherapeutic tumor cell cytotoxicity, and exhibit no additional toxicity beyond that of Abraxane® nanoparticles alone.

Example 7—Abraxane®/Avastin® Complexes Disassociate in Serum

The following was performed to determine what happens to Abraxane®/Avastin® complexes in serum over time. 6 mg or 8 mg of Avastin® were bound to Abraxane® for 30 minutes at room temperature. The complexes were incubated with serum for 15, 30, 45, or 60 minutes. After this incubation, the serum/complex solution was spun down at 10,000 rpm for 10 minutes at 4° C. The supernatants were collected, separated using gel electrophoresis, and analyzed via Western blotting with an anti-paclitaxel antibody and an HRP-conjugated secondary antibody.

Figure 18:
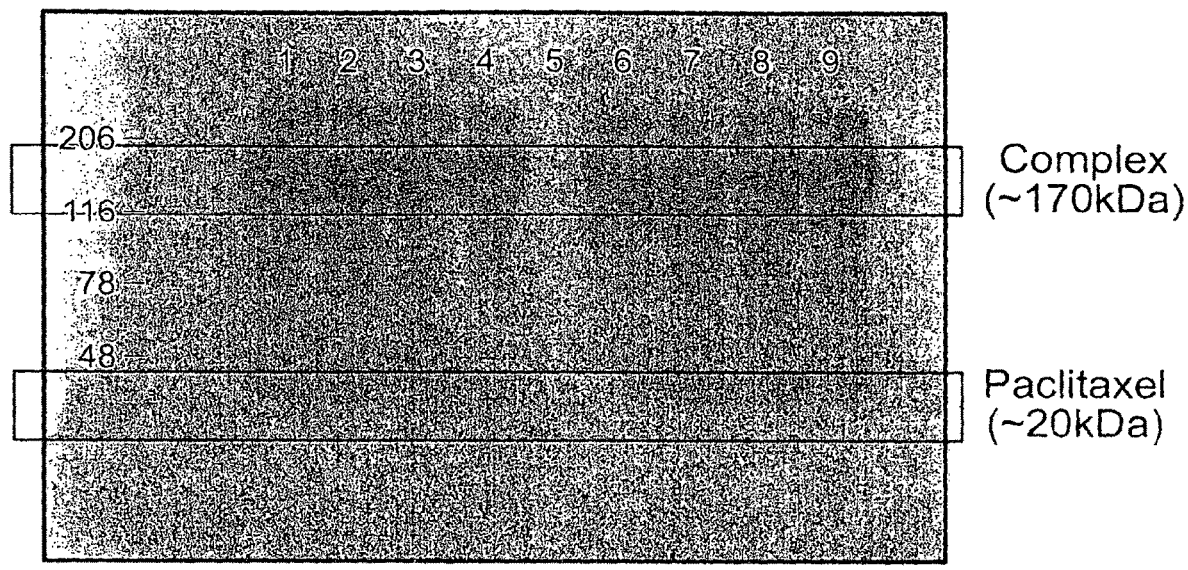
FIG. 18 is a photograph of a Western blot analysis of ABX:BEV complexes exposed to serum for 15, 30, 45, or 60 minutes. The ABX:BEV complexes were formed by incubating either 6 mg or 8 mg of BEV with ABX for 30 minutes at room temperature. The primary antibody used for the Western blot was an anti-paclitaxel antibody. Lane 1: ABX: BEV (6 mg) exposed to serum for 15 minutes; Lane 2: ABX: BEV (6 mg) exposed to serum for 30 minutes; Lane 3: ABX: BEV (6 mg) exposed to serum for 45 minutes; Lane 4: ABX: BEV (6 mg) exposed to serum for 60 minutes; Lane 5: blank; Lane 6: ABX: BEV (8 mg) exposed to serum for 15 minutes; Lane 7: ABX: BEV (8 mg) exposed to serum for 30 minutes; Lane 8: ABX: BEV (8 mg) exposed to serum for 45 minutes; Lane 9: ABX: BEV (8 mg) exposed to serum for 60 minutes.

Incubation in the presence of serum resulted in complex disassociation, not disintegration (FIG. 18).

Example 8—Bevacizumab does not Bind Free Paclitaxel

The following was performed to determine if bevacizumab binds free paclitaxel. 4 mg of bevacizumab was incubated with paclitaxel (0.1, 0.5, 1, or 2 mg) for 30 minutes at room temperature. After this incubation, the mixtures were separated using gel electrophoresis and analyzed via Western blotting with an anti-paclitaxel antibody and an HRP-conjugated secondary antibody.

Figure 19:
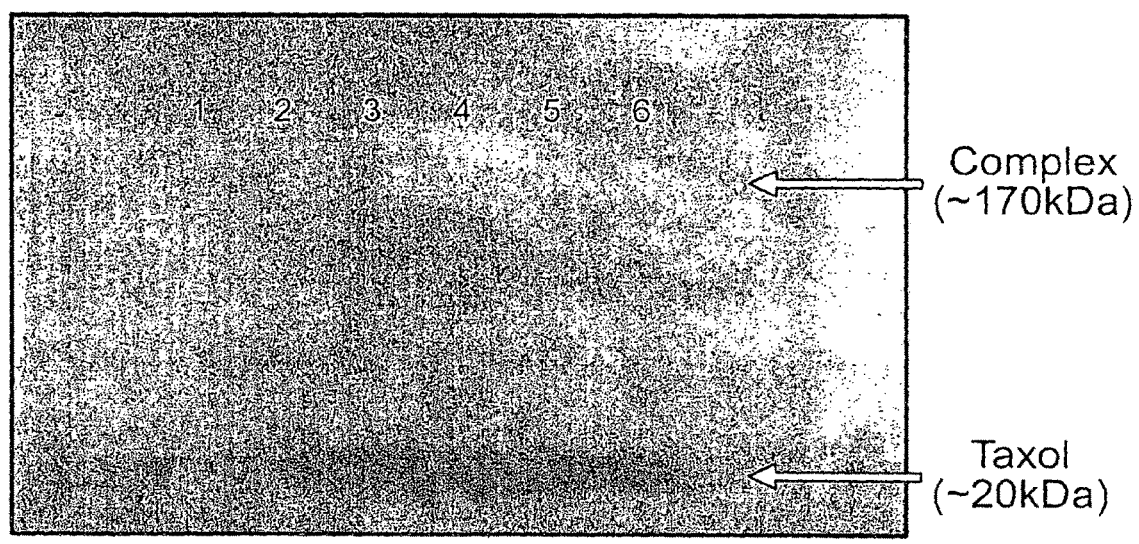
FIG. 19 is a photograph of a Western blot analysis of mixtures of paclitaxel (0.1, 0.5, 1, or 2 mg) and BEV (4 mg) incubated together for 30 minutes at room temperature. The primary antibody used for the Western blot was an anti-paclitaxel antibody. Lane 1: Bev (4 mg); Lane 2: Taxol (2 mg); Lane 3: Taxol (2 mg)+Bev (4 mg); Lane 4: Taxol (1 mg)+Bev (4 mg); Lane 5: Taxol (0.5 mg)+Bev (4 mg); Lane 6: Taxol (0.1 mg)+Bev (4 mg).

Bevacizumab did not bind free paclitaxel (FIG. 19).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a VEGF-expressing cancer in a mammal, which method comprises:
   (a) confirming that the cancer to be treated expresses VEGF;
   (b) obtaining a dry composition of preformed nanoparticle complexes comprising albumin-bound paclitaxel and an anti-VEGF antibody, wherein the ratio of albumin-paclitaxel to antibody is between 2:1 and 1:25, and wherein the anti-VEGF antibody is bevacizumab;
   (c) forming an aqueous composition of said dry composition, said aqueous composition being suitable far injection into a mammal having cancer, and
   (d) administering to said mammal an effective amount of the aqueous composition, wherein said administration treats said, cancer and wherein said preformed complexes retain antibody mediated VEGF binding specificity.

2. The method of claim 1, wherein said mammal is a human.

3. The method of claim 1, wherein said cancer is skin cancer.

4. The method of claim 3, wherein said skin cancer is stage IV melanoma.

5. The method of claim 1, wherein said dry composition comprises an alkylating agent.

6. The method of claim 1, wherein said injectable composition is administered intravenously.

* * * * *